(12) United States Patent
Clawson et al.

(10) Patent No.: US 6,415,788 B1
(45) Date of Patent: Jul. 9, 2002

(54) APPARATUS FOR TREATING RESPIRATORY GASES INCLUDING LIQUID TRAP

(75) Inventors: Burrell E. Clawson, Newport Beach, CA (US); James Weigl, Las Vegas, NV (US)

(73) Assignee: Enternet Medical, Inc., Las Vegas, NV (US)

( * ) Notice: Subject to any disclaimer, the term of this patent is extended or adjusted under 35 U.S.C. 154(b) by 0 days.

(21) Appl. No.: 09/347,603

(22) Filed: Jul. 2, 1999

(51) Int. Cl.⁷ .............................................. A61M 16/16
(52) U.S. Cl. ............................. 128/201.13; 128/205.12; 128/205.27
(58) Field of Search ...................... 128/201.13, 203.12, 128/203.15, 205.12, 205.25, 205.26, 205.27, 205.28, 205.29, 206.17, 206.22

(56) References Cited

U.S. PATENT DOCUMENTS

| | | |
|---|---|---|
| 3,721,238 A | 3/1973 | Wise et al. |
| 3,747,598 A | 7/1973 | Cowans |
| 3,782,081 A | 1/1974 | Munters |
| 3,932,153 A | 1/1976 | Byrns |
| 4,036,616 A | 7/1977 | Byrns |
| 4,040,804 A | 8/1977 | Harrison |
| 4,063,913 A | 12/1977 | Kippel et al. |
| 4,090,513 A | 5/1978 | Togawa |
| 4,108,172 A | 8/1978 | Moore, Jr. |
| 4,133,656 A | 1/1979 | Kippel et al. |
| 4,148,732 A | 4/1979 | Burrow et al. |
| 4,168,706 A | 9/1979 | Lovell |
| 4,171,962 A | 10/1979 | Kippel et al. |
| 4,172,709 A | 10/1979 | Kippel et al. |
| 4,181,511 A | 1/1980 | Kippel et al. |
| 4,181,512 A | 1/1980 | Kippel et al. |
| 4,200,094 A | 4/1980 | Gedeon et al. |
| 4,224,939 A | 9/1980 | Lang |
| 4,297,117 A | 10/1981 | Holter et al. |
| 4,360,018 A | 11/1982 | Choksi |
| 4,367,734 A | 1/1983 | Benthin |
| 4,458,679 A | 7/1984 | Ward |
| 4,516,573 A | 5/1985 | Gedeon |
| 4,558,696 A | * 12/1985 | Eiserman et al. ...... 128/205.12 |
| 4,597,917 A | 7/1986 | Lunsford |
| 4,687,235 A | 8/1987 | Stoll |
| 4,707,167 A | 11/1987 | Saito et al. |
| 4,771,770 A | 9/1988 | Artemenko et al. |
| 4,829,997 A | 5/1989 | Douwens et al. |
| 5,016,628 A | 5/1991 | Lambert |
| 5,022,394 A | 6/1991 | Chmielinski |
| 5,035,236 A | 7/1991 | Kanegaonkar |
| 5,038,767 A | 8/1991 | Jumpertz |
| 5,109,471 A | 4/1992 | Lang |
| 5,172,686 A | 12/1992 | Anthony |
| 5,195,527 A | 3/1993 | Hicks |
| 5,213,096 A | 5/1993 | Kihlberg et al. |
| 5,228,435 A | 7/1993 | Smith |
| 5,230,727 A | 7/1993 | Pound et al. |
| 5,255,674 A | 10/1993 | Oftedal et al. |
| 5,320,096 A | 6/1994 | Hans |
| 5,337,739 A | 8/1994 | Lehman |

(List continued on next page.)

FOREIGN PATENT DOCUMENTS

GB 2267840 * 12/1993

*Primary Examiner*—John G. Weiss
*Assistant Examiner*—Mital Patel
(74) *Attorney, Agent, or Firm*—Stout, Uxa, Buvan & Nullius, LLP; Frank J. Uxa

(57) ABSTRACT

Apparatus for treating respiratory gases include a housing having a patient side port adapted for connection to a tracheal tube device and a machine side port adapted for connection to a tube for passing respiratory gases; and one or more liquid trap chambers positioned between the patient side and machine side ports and adapted to receive and hold liquid passed from outside the housing through the patient side and machine side ports.

49 Claims, 9 Drawing Sheets

U.S. PATENT DOCUMENTS

| | | | |
|---|---|---|---|
| 5,360,002 A | 11/1994 | Smith | |
| 5,383,447 A | 1/1995 | Lang | |
| 5,386,825 A | 2/1995 | Bates | |
| 5,390,668 A | 2/1995 | Lehman | |
| 5,398,677 A * | 3/1995 | Smith | 182/205.12 |
| 5,435,298 A | 7/1995 | Anthony | |
| 5,435,299 A | 7/1995 | Langman | |
| 5,460,172 A | 10/1995 | Eckerbom et al. | |
| 5,462,048 A | 10/1995 | Lambert et al. | |
| 5,468,451 A | 11/1995 | Gedeon | |
| 5,482,031 A | 1/1996 | Lambert | |
| 5,487,382 A | 1/1996 | Bezicot | |
| 5,505,768 A | 4/1996 | Altadonna | |
| 5,546,930 A | 8/1996 | Wikefeldt | |
| 5,558,088 A | 9/1996 | Smith | |
| 5,570,684 A | 11/1996 | Behr | |
| 5,577,494 A | 11/1996 | Kuypers et al. | |
| 5,590,644 A | 1/1997 | Rosenkoetter | |
| 5,647,344 A | 7/1997 | Turnbull | |
| 5,715,815 A * | 2/1998 | Lorenzen et al. | 128/207.14 |
| 5,738,091 A * | 4/1998 | Kee et al. | 128/205.12 |
| 5,964,223 A * | 10/1999 | Baran | 128/207.14 |
| 5,992,413 A | 11/1999 | Martin, Jr. et al. | |
| 6,095,135 A * | 8/2000 | Clawson et al. | 128/201.13 |
| 6,105,576 A * | 8/2000 | Clawson et al. | 128/205.12 |
| 6,227,200 B1 * | 5/2001 | Crump et al. | 128/207.16 |

* cited by examiner

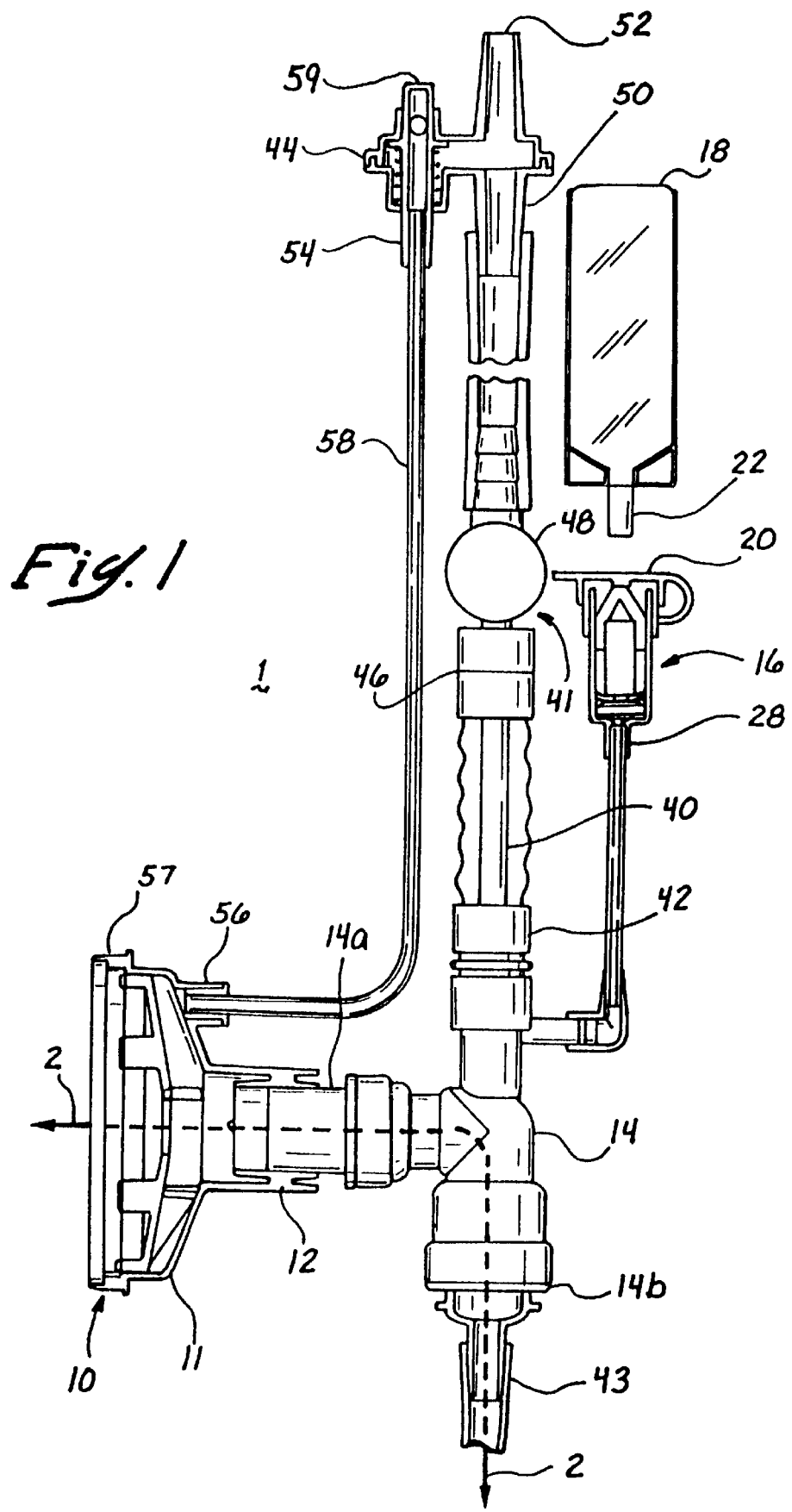

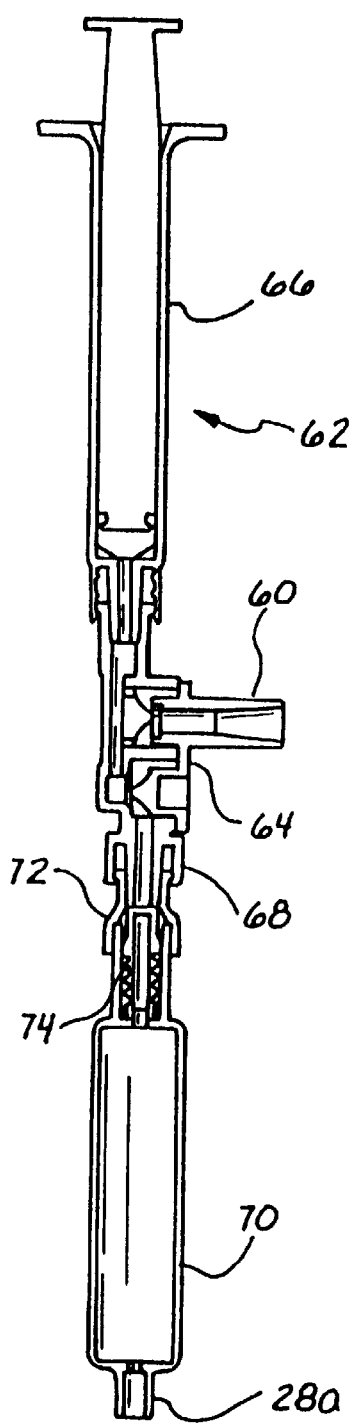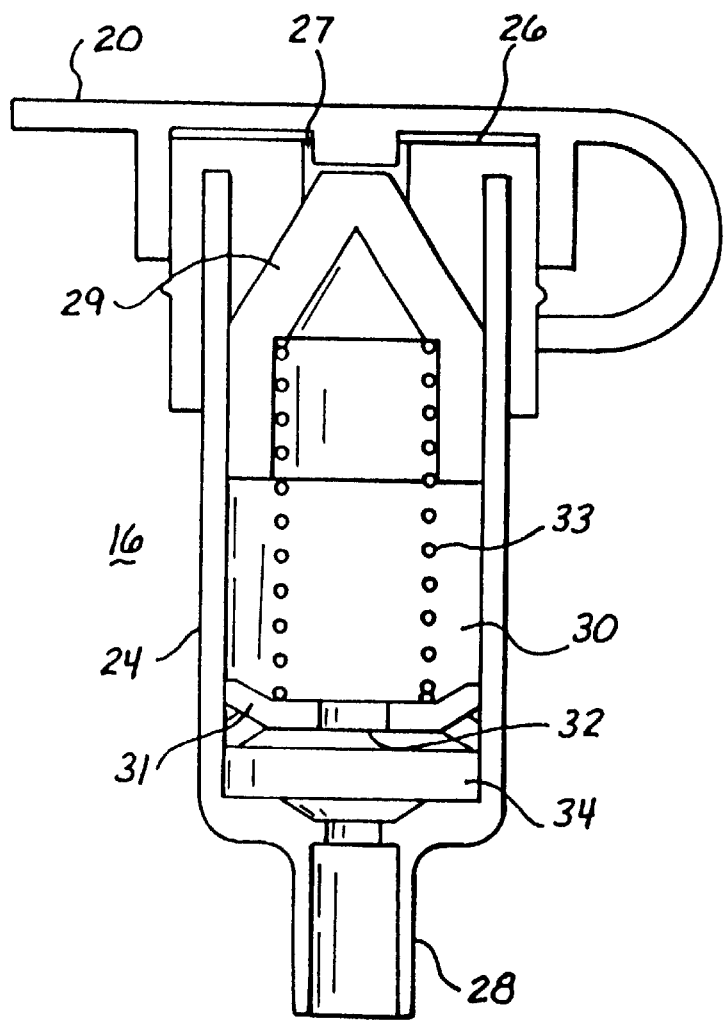

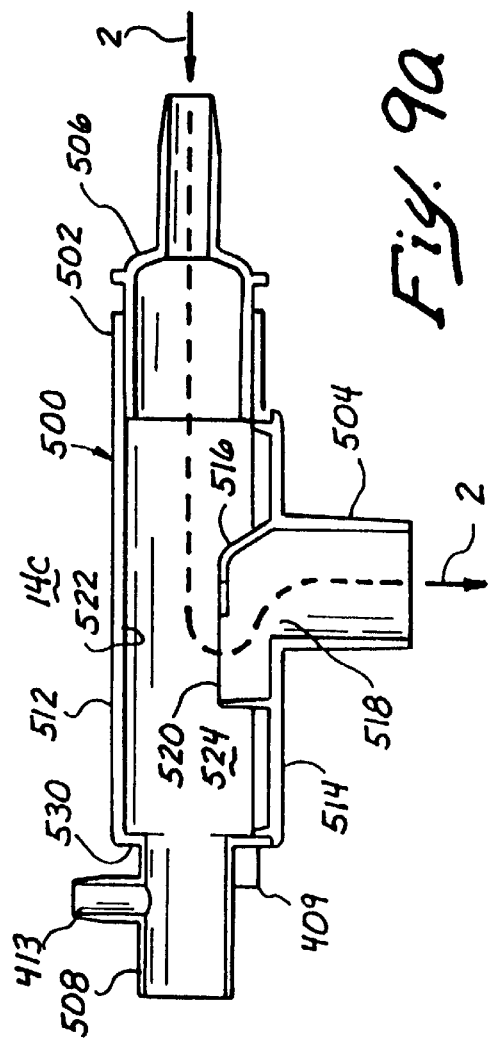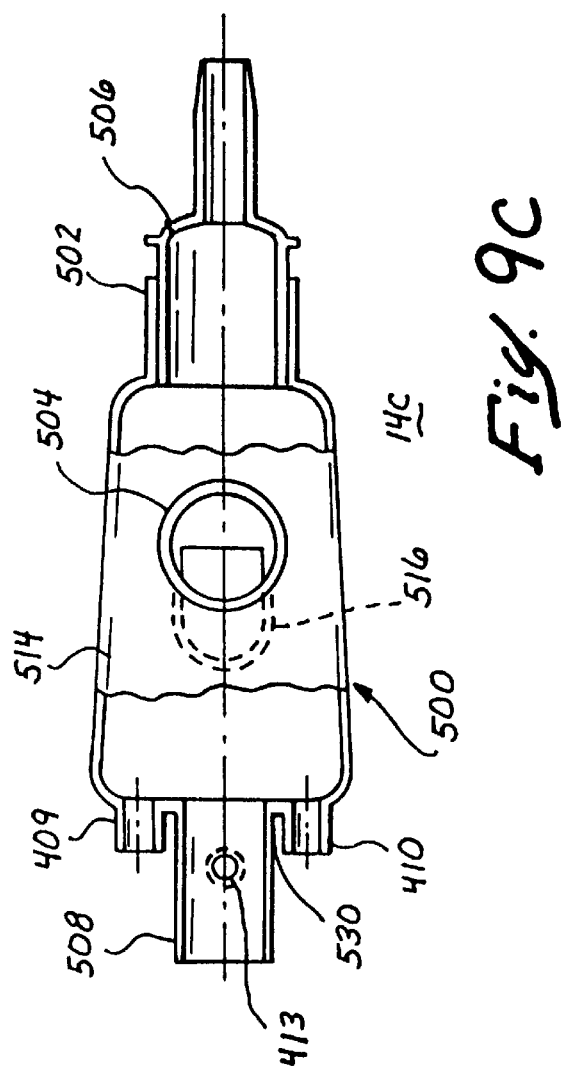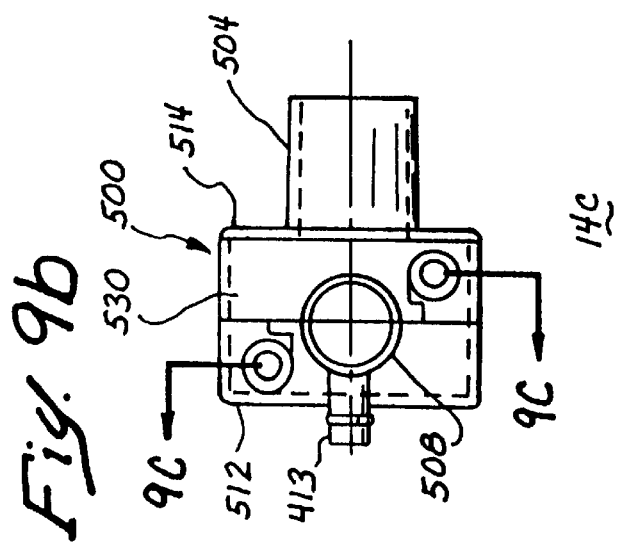

APPARATUS FOR TREATING RESPIRATORY GASES INCLUDING LIQUID TRAP

BACKGROUND OF THE INVENTION

1. Field of the Invention

The present invention relates to an apparatus useful for treating and handling both respiratory gases and liquids going both to and from the patient. More particularly, in the invention relates to an apparatus which includes liquid traps, suction valves, and a check valve that are preferably effective to protect one or more components of the apparatus from being clogged internally or contaminated through exposure to contaminants both internal and external to the apparatus.

2. Description of the Related Art

During surgery and other medical procedures, a patient is frequently connected to an anesthesia machine or ventilator to provide respiratory gases to the patient. The respiratory gases passed to the patient are advantageously filtered, heated and humidified so that the gases entering the patient are of a suitable quality, temperature and humidity so as to positively impact the patient. Heat and moisture exchangers (HMEs) are often used to provide heat and humidity to the respiratory gases entering the patient. Typically, these HMEs are located so that respiratory gases exhaled from the patient pass through a tracheal tube into the HME, including at least one fibrous or other gas permeable material, which accumulates or collects heat and moisture from the exhaled gases. A filter element, for example, an antimicrobial filter element, is often located in the HME to filter respiratory gases passing through the HME. During the inhalation of respiratory gases, for example, from a respiratory ventilator machine, the HME provides higher levels of heat and moisture to these respiratory gases prior to the gases entering the patient. Over a period of time, the HME is effective to maintain a certain level of temperature and humidity in the respiratory gases entering the patient.

Although such HMEs do perform effectively to provide at least some of the useful heat and humidity needed for respiratory gases under normal conditions, additional required patient treatments and/or patient expectorations may cause adverse effects to the HMES. One example of such an additional treatment is the use of saline or other aqueous liquids to loosen partially hydrated mucous secretions in the trachea of the patient. Mucous build-up is of particular concern in situations when the patient is an infant or neonate and/or in long term, for example, about six (6) hours or longer, use of a ventilator. Saline lavage is often used to counter such mucous buildup. Thus, saline or other aqueous solution is introduced through an inserted tracheal catheter to loosen mucous secretions in the trachea. If the clinician accidentally gets the aqueous solution sloshing back with an exhaled breath or does not suction it correctly in a timely manner, the liquid can fill up or block a good portion of the flow area of the HME and/or the HME's filter element, thereby drastically increasing the pressure required to pass respiratory gases back and forth. In this situation, the entire HME may have to be replaced in order to effectively allow respiratory gases to pass to and from the patient. Such HME replacement is an emergency and can be disruptive and/or harmful to the patient and/or can cause additional clinician stress, in addition to opening up the patient's breathing circuit to external contaminants.

Respiratory gas circuits can include a humidifier and a filter located between the patient and the ventilator. Such circuits are of particular value in treating infants and neonates, for example, with lung volumes on the order of about 10 cubic centimeters. However, liquid water can condense in the tubing from the humidifier and be "blown" or carried to the filter, where such liquid can cause increased pressure drop causing non-optimal ventilation and disadvantageously making for more difficult or impossible respiration.

A patient's health is compromised by the introduction of pathogens on dust and other foreign matter into the HME on the patient side of the bacteria filter. The pathogens and foreign matter can invisibly foul the HME filter or treatment unit rendering it ineffective for its desired purpose. The pathogens and other foreign matter are often introduced by exposing the interior of the respiratory equipment to atmospheric air. The interior of the respiratory circuit is exposed to the atmosphere when suction ports connected to the liquid traps are opened to attach a suction conduit thereto and/or the HME filter is replaced frequently or unplugged from the endotracheal suction manifold to drain the liquid manually. The tracheal tube is also exposed to atmospheric air when a port in the endotracheal suction manifold is opened to introduce saline solution to the trachea during a tracheal lavage. The exposure of the interior of the respiratory apparatus components to pathogens and other foreign matter results the patient's lungs being exposed to the contaminants during respiration through the unit.

The decrease in the useful life of the HME unit is costly and not beneficial to the patient in several ways. A shorter useful life of the HME unit results in more units needed to treat a patient, more chances for pathogen contamination, more clinician work, more physical and mental stress on the patient, and an increase in cost of the patient's medical care. The increased exposure to bacteria and other foreign matter results in increased opportunity for respiratory system infections and other detrimental medical situations, as is disclosed in U.S. Pat. No. 4,224,939 to Lang entitled BACTERIA-TIGHT SYSTEM FOR ARTIFICIAL RESPIRATION, which is incorporated herein by reference in its entirety.

It would be advantageous to provide apparatus by which respiratory gases can be effectively and reliably treated and which can be protected against liquid material interfering with such treatment, causing problems with the respiration of the patient, and restricting the exposure of the interior respiratory equipment to the external ambient room atmosphere and its inevitable contamination.

SUMMARY OF THE INVENTION

An apparatus for treating the respiratory gases of a patient has been discovered. The apparatus comprises a housing with a patient side port, a machine side port, two or more liquid trap chambers, a treatment chamber, and a wall. The patient side port is adapted for passing respiratory gases between the housing and the patient. The machine side port is adapted for passing respiratory gases between the housing and a respiration machine. The liquid trap chambers are adapted to receive liquid. The treatment chamber contains a treatment component adapted to provide a benefit to the respiratory gases passing therethrough. The patient side and machine side ports, the treatment chamber, and the liquid trap chambers are positioned to define a respiratory flow path through the housing passing between the patient side and machine side ports and through the treatment chamber and the liquid trap chambers. The wall has one or more openings through which liquid is removable from the liquid trap chambers. The openings are spaced apart from the patient and machine side ports.

In an aspect of the invention, the liquid trap chambers are configured to inhibit liquid passed from outside the housing through the patient side port from entering the treatment chamber.

In an aspect of the invention, the liquid trap chambers are sized and positioned to hold liquid passed from outside the housing through the patient side port.

In an aspect of the invention, the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water and/or heat available to humidify respiratory gases passing through the housing; (4) a hygroscopic component adapted to generate heat available to heat respiratory gases passing through the housing; (5) porous thermal mass heat exchanger material with high surface area; and (6) combinations thereof.

In an aspect of the invention, at least one of the liquid trap chambers is sized and positioned to collect liquid between the treatment chamber and the patient side port.

In an aspect of the invention, at least one of the liquid trap chambers is sized and positioned to collect liquid between the treatment chamber and the machine side port.

In an aspect of the invention, a first liquid trap chamber is sized and positioned to collect liquid between the treatment chamber and the patient side port. Further, a second liquid trap chamber is sized and positioned to collect liquid between the treatment chamber and the machine side port. In a further aspect of the invention, a third liquid trap container is sized and positioned to collect liquid between the treatment chamber and the first liquid trap chamber. In a still further aspect of the invention, a baffle is disposed between the first and third liquid trap chambers. The baffle may be of an annular shape.

In an aspect of the invention, the treatment chamber further comprises a gas flow bypass extending through the treatment chamber, wherein the gas flow bypass is linearly aligned with the patient side port. In a still further aspect of the invention, a check valve is in fluid communication with the gas flow bypass. The check valve is adapted to inhibit gas flow from the machine side port, through the gas flow bypass, and to the patient side port. The check valve is further adapted to enable a portion of gas flow and/or liquid from the patient side port to flow through the gas flow bypass and towards the machine side port, with the remainder of the gas flow from the patient side port being directed through the treatment chamber. In a still further aspect of the invention, a baffle is disposed between the patient side port and the treatment chamber, wherein the patient side port, the gas flow bypass, and a hole in the baffle are linearly aligned. In a further aspect of the invention, the check valve is a leaf check valve.

The discovered invention is also embodied in an apparatus for treating the respiratory gases of a patient. The apparatus comprises a housing and a suction assembly. The housing comprises with a patient side port, a machine side port, one or more liquid trap chambers, a treatment chamber, and a wall. The patient side port is adapted for passing respiratory gases between the housing and the patient. The machine side port is adapted for passing respiratory gases between the housing and a respiration machine. The liquid trap chambers are adapted to receive liquid. The treatment chamber contains a treatment component adapted to provide a benefit to the respiratory gases passing therethrough. The patient side and machine side ports, the treatment chamber, and the liquid trap chambers are positioned to define a respiratory flow path through the housing passing between the patient side and machine side ports and through the treatment chamber and the liquid trap chambers. The wall has one or more openings through which liquid is removable from the liquid trap chambers, wherein the openings are spaced apart from the patient and machine side ports. The suction assembly is in fluid communication with the one or more openings. The suction assembly is adapted to remove liquid from the liquid trap chamber without exposing the respiratory flow path through the housing to the ambient atmosphere.

In an aspect of the invention, the suction assembly comprises a suction manifold comprising one or more inlets in fluid communication with the one or more liquid trap chambers, respectively, and an outlet adapted for connection to a suction source. The suction assembly also comprises valves that are disposed between the wall openings and the suction manifold outlet, wherein the valves are adapted to control suction through the wall openings.

In an aspect of the invention, the liquid trap chambers are configured to inhibit liquid passed from outside the housing through the patient side port from entering the treatment chamber.

In an aspect of the invention, the liquid trap chambers are sized and positioned to hold liquid passed from outside the housing through the patient side port.

In an aspect of the invention, the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water and/or heat available to humidify respiratory gases passing through the housing; (4) a hygroscopic component adapted to generate heat available to heat respiratory gases passing through the housing; (5) porous thermal mass heat exchanger material with high surface area; and (6) combinations thereof.

In an aspect of the invention, at least one of the liquid trap chambers is sized and positioned to collect liquid between the treatment chamber and the patient side port.

In an aspect of the invention, at least one of the liquid trap chambers is sized and positioned to collect liquid between the treatment chamber and the machine side port.

In an aspect of the invention, a first liquid trap chamber is sized and positioned to collect liquid between the treatment chamber and the patient side port. Further, a second liquid trap chamber is sized and positioned to collect liquid between the treatment chamber and the machine side port. In a further aspect of the invention, a third liquid trap container is sized and positioned to collect liquid between the treatment chamber and the first liquid trap chamber. In a still further aspect of the invention, a baffle is disposed between the first and third liquid trap chambers. The baffle may be of an annular shape.

In an aspect of the invention, the treatment chamber further comprises a gas flow bypass extending through the treatment chamber, wherein the gas flow bypass is linearly aligned with the patient side port. In a still further aspect of the invention, a check valve is in fluid communication with the gas flow bypass. The check valve is adapted to inhibit gas flow from the machine side port, through the gas flow bypass, and to the patient side port. The check valve is further adapted to enable a portion of gas flow from the patient side port to flow through the gas flow bypass and towards the machine side port, with the remainder of the gas flow from the patient side port being directed through the treatment chamber. In a still further aspect of the invention, a baffle is disposed between the patient side port and the treatment chamber, wherein the patient side port, the gas flow bypass, and a hole in the baffle are linearly aligned. In a further aspect of the invention, the check valve is a leaf check valve.

The discovered invention is also embodied in a system for treating the respiratory gases of a patient. The system comprises a liquid trap and a device comprising a respiratory gas treatment chamber. The liquid trap comprises a trap housing and a trap chamber. The trap housing has a patient side port being adapted for fluid communication with a tracheal tube device, and a machine side port being adapted for fluid communication with a device comprising a respiratory gas treatment chamber. The trap chamber is positioned in the trap housing between the patient side port and the machine side port. The trap chamber is adapted to receive liquid. The liquid trap housing does not contain a filter or other respiratory gas treatment chamber. The device comprising the respiratory gas treatment chamber is similar, if not the same, as other devices describe herein. The machine side port of the trap housing is in fluid communication with a patient side of the device comprising the respiratory gas treatment chamber. The trap housing is spaced apart from the housing of the device comprising the respiratory gas treatment chamber.

In an aspect of the invention, the system further comprises a suction assembly in fluid communication with an opening in a wall of the trap housing through which liquid in the trap is removable via the suction assembly without exposing the respiratory flow path through the trap housing to ambient atmosphere.

In an aspect of the invention, the trap housing comprises a wall having an opening through which liquid is removable from the trap chamber. Further, the system comprises a suction manifold and a valve. The suction manifold has an inlet in fluid communication with the trap chamber and an outlet adapted for connection to a suction source. The valve is disposed between the wall opening and the suction manifold outlet, wherein the valve is adapted to control suction through the wall opening.

In an aspect of the invention, the liquid trap further comprises a baffle disposed in the trap housing. The baffle is adapted to be impinged upon by a respiratory gas flow passing between the patient side port and the machine side port and through the trap housing. In a further aspect of the invention, the baffle comprises a blocking member positioned in a direct path between the patient side port and the machine side port.

In a still further aspect of the invention, the suction assembly is adapted to facilitate periodic removal of liquid from the device liquid trap chambers and the trap chamber of the liquid trap without exposing the device liquid trap chambers and the trap chamber of the liquid trap to the atmosphere outside of the device and the liquid trap.

In a still further aspect of the invention, the suction assembly is adapted to facilitate periodic removal of liquid from the device liquid trap chambers and the trap chamber of the liquid trap without separating the suction manifold from the device wall openings and the liquid trap wall opening.

The discovered invention is also embodied in a respiratory gas treatment system comprising an endotracheal suction manifold comprising a device port, a patient side port, a machine side port, a liquid trap, and a wall. The device port is adapted for connection with a respiratory treatment device. The patient side port is adapted for passing respiratory gases between the endotracheal suction manifold and the patient. The machine side port is adapted passing respiratory gases between the endotracheal suction manifold and a respiration machine. The liquid trap is adapted to receive liquid. The patient side port, the machine side port, and the liquid trap are positioned to define a respiratory flow path through the endotracheal suction manifold passing between the patient side and machine side ports and through the liquid trap. The wall has an opening through which liquid is removable from the liquid trap, wherein the opening is spaced apart from the patient side port and the machine side port.

In an aspect of the invention, a suction catheter assembly is functionally connected to the device port.

In an aspect of the invention, a medication delivery apparatus, a metered dosed inhaler, or a nebulizer is functionally connected to the device port.

In an aspect of the invention, the system further comprises an apparatus for use during tracheal lavages functionally connected to the device port. The apparatus comprises a housing and a microbial filter. The housing has a first port and a second port, the first port being adapted to receive a lavaging liquid, the second port being adapted to be in fluid communication with a tracheal tube in fluid communication with the patient side port. The microbial filter is disposed in the housing. The first and second ports and the microbial filter are positioned so that gas or lavaging liquid passes from the first port to the second port and through the microbial filter.

In an aspect of the invention, the system further comprises a suction manifold and a valve. The suction manifold comprises an endotracheal inlet and an outlet. The endotracheal inlet is in fluid communication with the liquid trap. The outlet is adapted for connection to a suction source. The valve is disposed between the wall opening and the suction manifold outlet, wherein the valve is adapted to control suction through the wall opening.

In a still further aspect of the invention, the system further comprises an apparatus for treating the respiratory gases of a patient. The apparatus comprises a housing comprising a housing patient side port, a housing machine side port, a treatment chamber, a housing liquid trap, and a housing wall. The housing patient side port is functionally connected to the machine side port of the endotracheal suction manifold. The housing patient side port is adapted for passing respiratory gases between the housing and the patient. The housing machine side port is adapted for passing respiratory gases between the housing and the respiration machine. The treatment chamber contains a treatment component adapted to provide a benefit to the respiratory gases passing therethrough. The housing liquid trap is adapted to receive liquid from the respiratory gases passing therethrough. The housing patient side port, the housing machine side port, the housing treatment chamber, and the housing liquid trap are positioned to define a respiratory flow path through the housing passing between the housing patient side and housing machine side ports and through the treatment chamber and the housing liquid trap. The housing wall has an opening through which liquid is removable from the housing liquid trap. The suction manifold further comprises an apparatus inlet in fluid communication with the housing liquid trap through the housing wall opening. The system further comprises an apparatus valve disposed between the housing wall opening and the suction manifold outlet, wherein the apparatus valve is adapted to control suction through the housing wall opening.

The discovered invention is also embodied in a swivel fitting for use in respiratory gas flow connections to treatment devices. The swivel fitting comprises a female part, a male part, and a circumferential bead. The female part comprises an interior surface that defines a passage extending through the female part. The male part comprises an exterior surface and an interior surface, wherein the exterior surface complements at least a portion of the female part interior passage and the interior surface defines a gas flow passage extending therethrough. The circumferential bead extends outward from the male part exterior surface, the bead defining a plane that is normal to an axis extending along the gas flow passage. The bead and the female part exterior surface are adapted such that upon insertion of the male part into the female part passage, the bead forms a bead deformation undercut in the female part interior surface, thereby creating and maintaining a seal between the male part exterior surface and the female part interior surface and a retaining force to inhibit axial movement.

In an aspect of the invention, the female part interior surface and the male part exterior surface have a taper of less than two degrees per side.

In an aspect of the invention, the swivel fitting is installed in a device having an interior gas pressure of approximately two psi gauge.

In an aspect of the invention, the female part passage is in fluid communication with a wall opening a wall of a respiratory gas treatment device housing. Additionally, the male part gas flow passage is in fluid communication with an inlet of a suction manifold.

In an aspect of the invention, the swivel fitting forms a fluid connection between a respiratory gas treatment device and another respiratory gas treatment device.

In an aspect of the invention, the female part is comprised of a material that is softer than the bead. In a further aspect of the invention, the female part comprises a butadiene/styrene mixture and the bead comprises acrylic, acrylic-butadiene/styrene mixture, or polycarbonate.

The discovered invention is also embodied in an apparatus for use during tracheal lavages. The apparatus comprises a housing and a microbial filter. The housing has a first port and a second port, the first port being adapted to receive a lavaging liquid, and the second port being adapted to be in fluid communication with a tracheal tube. The microbial filter disposed in the housing, wherein first and second ports and the microbial filter are positioned so that gas or lavaging liquid passes from the first port to the second port and through the microbial filter.

In an aspect of the invention, the second port is in fluid communication with a suction catheter assembly.

In an aspect of the invention, the second port is in fluid communication with an endotracheal suction manifold.

In an aspect of the invention, the first port comprises a Luer check valve.

In an aspect of the invention, the first port is adapted to receive a nozzle of a squeezable container or a bulk container.

The discovered invention is also embodied in a method for providing respiratory gases to a patient comprising the step of providing a closed container which contains an apparatus as described above. The closed container is then opened. A suction assembly of the apparatus is placed in fluid communication with a suction source. A patient side port of the apparatus is placed in fluid communication with a patient. A machine side port of the apparatus is placed in fluid communication with a respiration machine.

In an aspect of the invention, a step of identifying a liquid-containing liquid trap chamber from the one or more liquid trap chambers adapted to receive liquid is performed. Next, liquid from the liquid-containing liquid trap chamber is suctioned out of the chamber using the suction assembly. The process is repeated as needed without exposing the liquid traps chambers to the atmosphere.

In an aspect of the invention, an auxiliary liquid trap chamber is installed between the patient side port and the patient such that the apparatus and the auxiliary liquid trap chamber is in fluid communication with the patient. The auxiliary liquid trap chamber is spaced apart from the apparatus housing.

In an aspect of the invention, a combined endotracheal suction manifold/fluid trap is installed between the patient side port and the patient such that the apparatus and the endotracheal suction manifold/fluid trap is in fluid communication with the patient.

The invention, together with the additional features and advantages thereof may best be understood by reference to the following description taken in connection with the accompanying illustrative drawings.

BRIEF DESCRIPTION OF THE DRAWINGS

FIG. 1 is a schematic view of an embodiment of the invention that comprises a microbial filter to treat tracheal lavage fluid.

FIG. 2 is a detail side cross section of a port containing the microbial filter of the invention shown in FIG. 1.

FIG. 3 is detail side cross section of a saline lavage pump and microbial filter that is an alternative embodiment of the microbial filter shown in FIG. 1.

FIG. 9a is a cross section view of the endotracheal suction manifold/fluid trap shown in FIG. 8.

FIG. 9b is an end view of the endotracheal suction manifold/fluid trap shown in FIG. 8.

FIG. 9c is a cross section view of the endotracheal suction manifold/fluid trap as taken through line 9c—9c shown in FIG. 9b.

DESCRIPTION OF THE PREFERRED EMBODIMENTS

Figure 4:
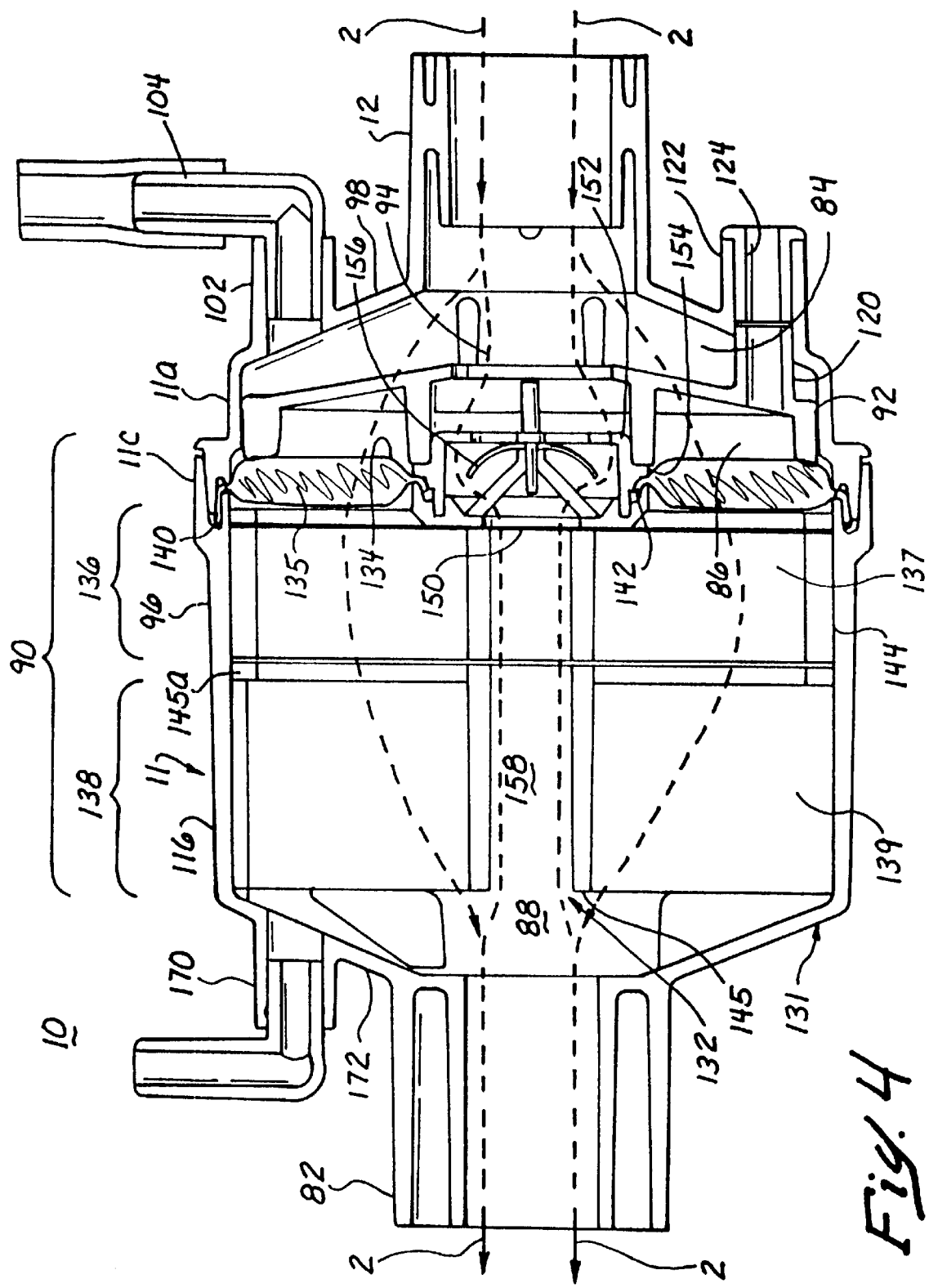
FIG. 4 is a side cross section view of a heat and moisture exchange unit according to an embodiment of the invention.

With reference to FIG. 1, a heat and moisture exchange (HME) unit 10, an endotracheal or ET elbow fitting 14, a suction catheter assembly 41, and a suction manifold 44 comprise a respiratory treatment apparatus 1 that permits removal of mucous, blood, and other fluids (referred collectively and interchangeably herein as "mucous", "liquid", or "fluid") from the apparatus without exposing a respiratory flow path 2 extending therethrough to contaminants in the atmosphere or from other sources, such as saline lavages. The contaminants may be bacteria and other foreign material. By reducing or eliminating the exposure of the flow path 2 to contaminants, the opportunity of infecting the patient is reduced and the useful life of the HME unit 10 is increased.

The HME unit 10 is comprises a housing 11 with a patient side port 12 extending from the housing. The patient side port 12 is connected to a machine side opening 14a of the ET elbow fitting 14 such that the HME unit 10 and the ET elbow fitting 14 is in fluid communication. Other embodiments of the invention may incorporate any other suitable device in place of the ET elbow fitting 14 to provide fluid communication between the HME unit 10 and the tracheal tube 43. An example of such a suitable device is an endotracheal suction manifold that functions to place the tracheal tube and the HME unit in fluid communication and functions to enable fluid communication with other devices, such as a medication delivery apparatus, a metered dosed inhaler, or a nebulizer.

By the ET elbow fitting 14 and the HME unit being in fluid communication, the respiratory flow path 2 extends between the unit and the elbow. A patient side opening 14b in the ET elbow fitting 14 is in fluid communication with a tracheal tube 43 that is inserted into the trachea of the patient (not shown). Embodiments of the invention may use any suitable ET elbow fitting, an example of which is disclosed in U.S. Pat. No. 5,694,922 to Palmer entitled SWIVEL TUBE CONNECTIONS WITH HERMETIC SEALS, which is incorporated by reference herein in its entirety.

While the tracheal tube 43 is inserted in patient, mucous may accumulate in the trachea, necessitating a tracheal lavage. The lavage assists in loosening and removing the accumulated mucous. The tracheal lavage comprises delivering saline or other solution (referred collectively herein as saline) to a port 16 that is in fluid communication with the ET elbow fitting 14. The saline solution is in a squeeze container 18 in the shown embodiment of the invention. Other embodiments of the invention may use any suitable container for providing saline for the tracheal lavage, an example of which is disclosed in U.S. Pat. No. 5,333,761 to Davis et al. entitled COLLAPSIBLE BOTTLE, which is incorporated herein by reference in its entirety. A cap 20 is removed from the port 16 and a nozzle 22 of the squeeze container 18 is inserted into the port. The saline is directed into the ET elbow fitting 14, out through the patient side opening 14b, and into the tracheal tube 43. A suction catheter 40 removes at least a portion of the saline/mucous from the patient's trachea through suction as described below.

Referring now to FIG. 2 as well, the port 16 is comprised of a housing 24 having an inlet end 26, shown at the top of FIG. 2, and an outlet end 28, shown at the bottom of FIG. 2. The cap 20 is removed from the inlet 26, exposing an inlet hole 27. The inlet hole 27 is sealed by a sealing member 29 disposed in the port interior 30. Also disposed in the port interior 30 is a microbial filter 34 that is urged against the outlet end 28 by a filter supporter 31. The filter supporter 31 has a centrally located hole 32 therethrough to enable the saline to flow through the filter supporter 31, through the filter 34 and out through the housing outlet 28. The sealing member 29 is urged against the inlet hole 27 by a spring 33 disposed between the sealing member and the filter supporter 31.

To flow saline through the port 16, the squeeze container nozzle 22 is inserted through the inlet hole 27, thereby translating the sealing member 29 towards the outlet end 28 and unsealing the inlet hole. The port 16 is designed and arranged such that when the sealing member 29 is translated away from inlet hole 27, the inlet hole is in fluid communication with the housing outlet 28. By being in fluid communication, the saline or other solution flows from the inlet hole 27, through the port interior 30, through the filter 34, and out through the housing outlet 28. The housing outlet 28 is in fluid communication with the ET elbow fitting 14. In other embodiments of the invention, the housing outlet may be in fluid communication with an endotracheal suction manifold or with an endotracheal suction manifold/liquid trap as disclosed below.

The port 16 has a microbial filter 34 that inhibits the introduction of contaminants to the respiratory flow path 2 from either the atmosphere or the saline solution. The microbial filter 34 inhibits the introduction of atmospheric contaminants into the respiratory apparatus 1 when the port 16 is open and exposed to the atmosphere. The filter 34 also provides another means for cleansing the saline used in the lavage. The filter 34 is disposed between the exit orifice 32 and the housing outlet 28 such that the saline solution flows through the filter prior to delivery to the ET elbow fitting 14.

Prior to the tracheal lavage, the suction catheter 40 of a suction catheter assembly 41 is inserted through a suction catheter fitting 42 in the elbow 14 and a tracheal tube 43. In embodiments of the invention, the suction catheter assembly 41 remains inserted in the fitting 42, with the suction catheter 40 directed into the tracheal tube 43 during the lavage. After the saline solution in container 18 is directed into the port 16 to wash the patient's trachea and rehydrate the mucous, suction is then applied to the suction catheter 40 to remove the saline solution and mucous from the trachea. Examples of suction catheter assemblies are disclosed in U.S. Pat. No. 5,730,123 issued to Lorenzen et al. and entitled MEDICAL MULTIPLE ACCESS LOW DEAD SPACE ANTI-MICROBIAL ASPIRATING/VENTILATING CLOSED SYSTEM IMPROVEMENTS AND METHODS; U.S. Pat. No. 5,735,271 issued to Lorenzen et al. and entitled MULTIPLE ACCESS ADAPTORS FOR MONITORING, SAMPLING, MEDICATING, ASPIRATING, AND VENTILATING THE RESPIRATORY TRACT OF A PATIENT; U.S. Pat. No. 5,715,815 issued to Lorenzen et al. and entitled SHEATH STERILITY PRESERVATION FILTER AND SEAL FOR SUCTION CATHETERS; U.S. Pat. No. 5,611,336 issued to Page et al. and entitled SINGLE USE MEDICAL ASPIRATING DEVICE AND METHOD; U.S. Pat. No. 5,277,177 issued to Page et al. and entitled SINGLE USE MEDICAL ASPIRATING DEVICE AND METHOD; U.S. Pat. No. 5,246,012 issued to Strickland and entitled BRONCHOALVEOLAR LAVAGE CATHETER; U.S. Pat. No. 5,233,979 issued to Strickland and entitled METHODS AND APPARATUS FOR A MICRO-TRACHEAL CATHETER HUB ASSEMBLY; U.S. Pat. No. 5,230,332 issued to Strickland and entitled METHODS AND APPARATUS FOR A MICRO-TRACHEAL CATHETER HUB ASSEMBLY; U.S. Pat. No. 5,218,957 issued to Strickland and entitled MULTI -LAYERED TRANSTRACHEAL CATHETER; U.S. Pat. No. 5,165,420 issued to Strickland and entitled BRONCHOALVEOLAR LAVAGE CATHETER; U.S. Pat. No. 5,199,427 issued to Strickland and entitled MULTI-LAYERED TRANSTRACHEAL CATHETER; U.S. Pat. No. 5,207,643 issued to Davis and entitled MULTI-LUMEN-CATHETER FLOW VALVE SYSTEM; U.S. Pat. No. 5,133,345 issued to Lambert and entitled NEONATAL CLOSED SYSTEM FOR INVOLUNTARY ASPIRATION AND VENTILATION, AND METHOD; U.S. Pat. No. 5,158,569 issued to Strickland et al. and entitled CATHETER PLACEMENT LOCKING AND SEALING DEVICE; U.S. Pat. No. 5,107,829 issued to Lambert and entitled NEONATAL CLOSED SYSTEM FOR INVOLUNTARY ASPIRATION AND VENTILATION, AND METHOD; U.S. Pat. No. 5,065,754 issued to Jensen and entitled ASPIRATING CATHETER TUBE INSERTER; and U.S. Pat. No. 4,569,344 issued to Palmer and entitled ASPIRATING/VENTILATING APPARATUS AND METHOD, all of which are incorporated by reference herein in their entireties.

The suction that is applied to the suction catheter 40 during the tracheal lavage is from the suction manifold 44. An outlet 46 of the suction catheter 40 is connected to a first valve 48 in the shown embodiment. The valve 48 is connected to a suction catheter inlet 50 of the suction manifold 44. The suction manifold 44 also has an outlet 52 that is connected to a suction source (not shown).

When the valve 48 is opened, suction is applied to the catheter 40.

In the shown embodiment, the suction manifold 44 also has an HME unit inlet 54 that is in fluid communication with an opening 56 in a wall 57 of the housing 11 via a tube 58. A second value 48 is integral with the suction manifold 44 and controls suction applied to wall opening 56 via the tube 58. Other embodiments of the invention may have other arrangements to control suction through the wall opening 56, such as a valve functionally disposed in the tube 58, a pinch valve disposed on the outside of the tube, or a valve incorporated into the wall opening 56. For the purposes defining the limitations of the claims, the tube 58 may be considered part of the suction manifold 44.

The applied suction removes mucous proximate the wall opening 56 of the HME unit 10 when the valve 59 is opened. Other embodiments of the invention with other means for suctioning mucous out of the HME unit 10 are discussed below.

Referring now to FIG. 3, in another embodiment of the invention, the saline solution may come from a bulk container, such as a bag or a bottle (not shown). The bulk container is in fluid communication with an inlet port 60 of a removable saline feed pump 62. The saline feed pump 62 has a double check valve assembly 64, syringe 66, and an outlet 68.

The saline solution from a bulk container passes through a microbial filter assembly 70 prior to being delivered to the ET elbow fitting 14. The microbial filter 70 has an inlet 72 that is in fluid communication with the saline feed pump outlet 68. In the shown and preferred embodiment of the invention, the filter assembly inlet 72 comprises a check valve Luer fitting 74. The check valve Luer fitting 74 comprises a flush surface when closed to minimize particle and other foreign matter pickup. Further, the fitting 74 is swabable with antiseptic to improve sanitation before connecting the filter assembly inlet 72 to the pump 62. In a preferred embodiment of the invention, the check valve Luer fitting 74 is available through Alaris Medical Systems, Inc., 10221 Wateridge Circle, San Diego, Calif. 92121-2733. When the pump 62 is used, the saline or other solution is pumped through the filter 70 and out a filter outlet 28a.

During delivery of the bulk saline or other solution to the patient's trachea, the filter outlet 28a is in fluid communication with an ET elbow fitting, such as ET elbow fitting 14 in FIG. 1. Other embodiments of the invention may use the syringe 66 filled with saline solution connected to the Luer fitting 74 of the filter assembly 70 without the double check valve assembly 64. Further embodiments of the invention may use a squeeze bottle with a Luer size outlet tip to deliver the saline solution through the filter 70. Additional embodiments of the invention comprise any suitable filtering device for receiving and passing the saline solution through a microbial filter prior to the tracheal lavage, with the filter being directly or indirectly attached to the ET elbow fitting 14 such that atmosphere may not directly enter the ET elbow fitting through the filtering device.

Referring now to FIG. 4, the HME unit 10 is comprised of a cylindrical housing 11 from which extends in opposing directions the patient side port 12, shown to the right, and a machine side port 82, shown to the left.

In other embodiments of the invention, the housing 11 may be of any suitable shape. The patient side port 12 receives respiration from the patient and directs respiration gas to the patient. The machine side port 82 receives gas from any suitable respiration machine used in respiratory treatment(not shown) and directs respiration from the patient to the respiration machine.

The HME unit 10 comprises three liquid trap chambers 84, 86, and 88 and a treatment chamber 90 disposed in the housing 11. The patient side port 12, the machine side port 82, the treatment chamber 90, and the first, second, and third liquid trap chambers 84, 86, and 88 are positioned so that the respiratory flow path 2 passing through the housing 11 passes between the patient side port and machine side port and through the treatment chamber and the liquid trap chambers.

The first and second liquid trap chambers 84 and 86 are disposed between the patient side port 12 and the treatment chamber 90. An annular baffle 92 defining a hole 94 extending therethrough separates the first and second liquid trap chambers 84 and 86, with the first liquid trap chamber 84 being proximate the patient side port 12. The annular baffle 92 extends radially inward from a cylindrical side wall 96 of the housing 11. The annular baffle hole 94 is axially centered in the housing 11 and generally axially aligned with the patient side port 12 and the machine side port 82. The first liquid trap chamber 84 is defined by a patient side end wall 98 of the housing 11, the housing side wall 96, and the baffle 92. The second liquid trap chamber 86 is defined by the baffle 92, the housing side wall 96, and the treatment chamber 90.

The function of the first and second liquid trap chambers 84 and 86 is to remove at least a portion of mucous from a patient's exhalation passing in the respiratory flow path 2 through the housing 11. More specifically, the portion of the mucous is removed from the exhalation as it passes from the patient side port 12 and before it reaches the treatment chamber 90. By removing the mucous prior to the exhalation passing through the treatment chamber 90, the useful life of the treatment chamber 90 is increased. The chamber 90 useful life is increased by reducing the contamination of it with 1) liquid; 2) fitting borne pathogens; and 3) air borne pathogens.

The mucous may be in the exhalation as a result of a patient with endotracheal tube receiving humidified air after a period of being respirated with relatively dry air. As the patient receives the relatively humidified air, the dry mucous in the trachea and lungs becomes moistened, loosens up, and may come up the tracheal tube. The mucous may clog or otherwise hinder the operation of the treatment chamber 90.

Referring now to FIG. 1 as well, another source for contamination of the treatment chamber 90 is the lavaged mucous and saline solution from the tracheal lavage. A portion of the lavaged mucous and saline solution may not be suctioned away by the suction catheter 40 during the lavage. The non-suctioned portion may be exhaled and enter the ET elbow fitting 14. From the ET elbow fitting 14, the non-suctioned portion may travel to the HME unit 10 and contaminate the treatment chamber 90 if not for the liquid trap chambers 84 and 86. For the purposes of description throughout the specification, "mucous", "liquid", and "fluid" shall encompass any substance besides respiration gas in the exhalation of the patient, including lavaged mucous, blood, saline solution, or any other liquid.

During use of the HME unit 10, a first portion of mucous in the patient's exhalation is removed as the exhalation passes through the first liquid trap chamber 84. A part of the first portion mucous falls out of the exhalation as the exhalation passes through the chamber 84. Another part of the first portion mucous is removed from the exhalation as the exhalation impinges on the baffle 92 or other surface defining the chamber 84 and entrained mucous deposits on the baffle. The exhalation then passes through the baffle hole 94 and into the second liquid trap chamber 86. A second portion of the mucous in the patient's exhalation is removed as the exhalation passes through the second liquid trap chamber 86.

Figure 5:
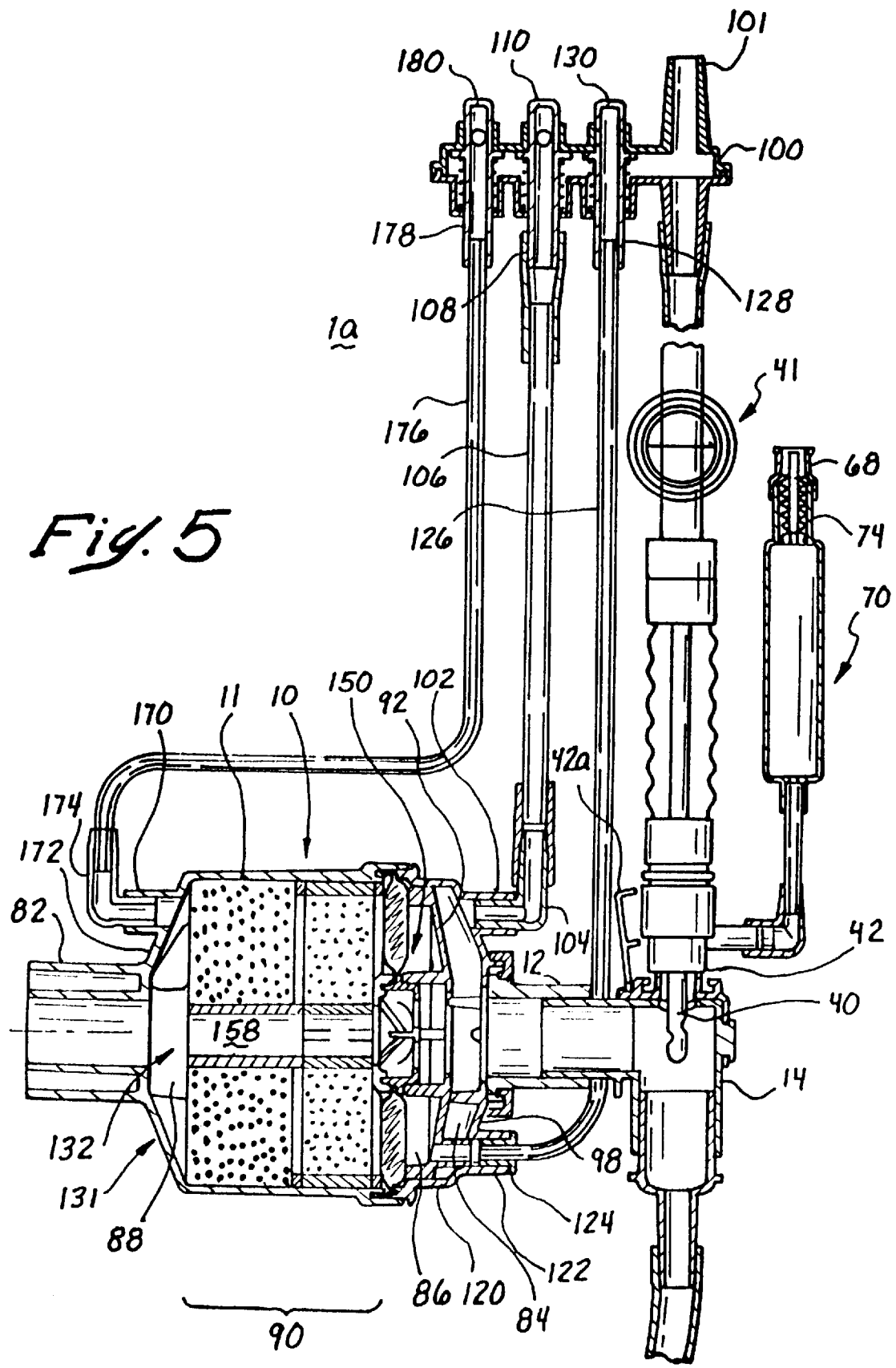
FIG. 5 is a side cross section view of the heat and moisture exchange unit shown in FIG. 4 attached to a suction manifold, an elbow fitting, a suction catheter assembly, and a microbial filter shown in FIG. 3 according to an embodiment of the invention.

Referring now FIG. 5 as well, the first, second and third liquid trap chambers 84, 86, 88 are in fluid communication with a suction manifold 100. The suction manifold 100 has an outlet 101 that is in fluid communication with a suction source (not shown). A first trap opening 102 extends through the patient side end wall 98. The first trap opening 102 has an elbow fitting 104 extending therefrom. A tube 106 makes a fluid connection between the elbow fitting 104 and a first suction inlet 108 in the suction manifold 100. When a third valve 110 in the suction manifold 100 is opened, suction is applied to the first trap opening 102 via the tube 106. The suction removes mucous present in the first liquid trap 84.

Suction is applied to the second liquid trap chamber 86 through a port 120 in the baffle 92. The port 120 fluidly connects the second liquid trap chamber 86 to a second trap opening 122 that extends through the patient side end wall 98. The second trap opening 122 has a tube bushing 124 inserted therein for receiving a tube 126. The tube 126 makes a fluid connection between second trap opening 122 and a second suction inlet 128 in the suction manifold 100. When a fourth valve 130 in the suction manifold 100 is opened, suction is applied to the second trap opening via the tube 126. The suction removes mucous present in the second liquid trap chamber 86.

The third liquid trap chamber 88 is for the removal of mucous and condensation from the HME unit 10. Inhalation gas being delivered to the machine side port 82 from a respiratory machine (not shown) may contain liquid vapor that condenses in the housing 11 but before entering the treatment chamber 90. Condensed vapor collected in any of the liquid trap chambers 84, 86, 88 is to be considered part of the "mucous" or "liquid" suctioned from the chambers. The third liquid trap chamber 88 collects the condensation. Further, mucous that has traveled through the treatment chamber 90 may also be present in the third liquid trap chamber 88.

Suction is applied to the third liquid trap chamber 88 through a port 170 in the machine side end wall 172 of the housing 11. The third trap opening 170 has an elbow fitting 174 extending therefrom. A tube 176 makes a fluid connection between the elbow fitting 174 and a third suction inlet 178 in the suction manifold 100. When a fifth valve 180 in the suction manifold 100 is opened, suction is applied to the third trap opening 170 via the tube 176. The suction removes condensation and mucous in the third liquid trap chamber 88.

The valves 110, 130, 180 are to the left of the suction manifold outlet 101. Other embodiments of the invention may have the valves 110, 130, and 180 arranged in any suitable manner. In a preferred embodiment of the invention, the valves 110, 130, 180 are biased to be closed. Embodiments of the invention may use any suitable valve or valves in the suction manifold. An embodiment of the invention may have the suction through the wall openings 102, 122, and 170 controlled by a manifold valve assembly that may comprise a single actuator (not shown). In an embodiment of the invention, the tubes and valves may be color coded or have indicia to assist in selecting the desired suction valve to open. In a further embodiment of the invention, the components of the HME unit 10 connected to the tubes may also be color coded in conjunction with the tubes and/or valves. Again, for the purposes of defining the limitations of the claims, the tubes may be considered a component of the suction manifold.

The first and second trap openings 102 and 122 are located proximate to each other in a preferred embodiment of the invention. The openings 102 and 122 are shown extending from opposing sides of the patient side end wall 98 for illustration purposes. The third trap opening 170 is also depicted where is it in relation to the housing 11 for illustration purposed only. In the preferred embodiment of the invention, the third trap opening 170 is approximately aligned with the first and second trap openings 102 and 122.

Referring to FIG. 4, the patient's exhalation enters the treatment chamber 90 of the HME unit 10 after passing through the first and second liquid trap chambers 84 and 86. The treatment chamber 90 comprises an annular gas treatment section 131 and an axially positioned exhalation bypass 132. The housing 11 is comprised of a patient side portion 11*a* and a machine side portion 11*b*. The portions 11*a* and 11*b* are bonded, thereby forming a joint 11*c*. The joined portions 11*a* and 11*b* define a portion of the cylindrical side wall 96. The bonding of the joint 11*c* may be of any suitable means, including adhesive bonding and ultrasonic bonding, that forms a leak-tight seal.

The annular gas treatment section 131 of the treatment chamber 90 comprises three stages 134, 136, and 138. The first stage 134 is located proximate the second liquid trap chamber 86. In a preferred embodiment of the invention, the first stage 134 comprises a bundled fibrous particle filter 135 with an electrostatic charge, such as "FILTRETE" trademark filters available from 3M. Other embodiments of the invention may have a particle filter without an electrostatic charge or may have a particle filter with antimicrobial activity. In the shown embodiment, the filter 135 is an annular with radial outer and inner extensions 140 and 142. The radial outer extension 140 is secured to the housing 11 by being crimped in the housing joint 11c. The radial inner extension 142 is crimped in an axially located check valve assembly 150 as described below.

The second stage 136 of the annular gas treatment section 131 is located between the first and third stages 134 and 138. The second stage 136 comprises a generating material 137, in particular, particulate carbon dioxide absorbing material. The generating material 137 is effective to generate both water and heat, preferably in response to an interaction with carbon dioxide, for example, absorption of and subsequent reaction with carbon dioxide, in the respiratory gas which comes in contact with the generating material. The carbon dioxide making up generating material 137 preferably is in the form of particles which are effective to absorb, or otherwise interact with, carbon dioxide in the respiratory gases. The generating material 137 preferably is sufficiently gas permeable so that respiratory gases passing therethrough result in a minimal pressure differential.

In a very useful embodiment, the amount of generating material present 137 is effective to generate only a portion, more preferably a minor portion (that is, no more than about 50%), of the water to humidify respiratory gases passing through the housing. In particular, the amount of generating material 137 present in the housing is effective to generate at least about 5%, more preferably at least about 10%, and still more preferably at least about 15% of the water to humidify respiratory gases passing through the housing. On the other hand, the amount of generating material present in the housing preferably is effective to generate no more than about 50% of the moisture of the water to humidify respiratory gases passing through the housing. Having excessively large amounts generating material present in the housing can result in the respiratory gases passing to the patient having a temperature which is excessively high relative to the requirements of the patient.

Although any suitable component or combinations of components may be useful in generating material 137 to generate moisture and heat, it is preferred that the generating material be that sold by W.R. Grace under the trademark "SODASORB".

It should be noted that the generating material 137 need not be present or may be replaced by an inert thermal storage mass and/or another HME element. None of the treating components within housing 11 are essential for practicing the invention. The treatment component or components can be selected to fit the needs of any given application. The third stage 138 of the annular gas treatment section 131 is located between the second stage 136 and the third liquid trap chamber 88. The third stage 138 comprises fibrous or cellular material 139 for absorbing heat and moisture during a patient's exhalation and releasing same to the patient on inhalation. The material 139 of the third stage 138 may also be referred to as the HME element 139.

A hygroscopic material coated on or embedded in the HME element 139 of the third stage 138 is very effective in assisting the HME unit 10 during initial or startup operation. The hygroscopic HME material comes in contact with water vapor from respiratory gases passing through the housing 11 and produces heat which is available for transfer to the respiratory gases being passed to the patient. As an alternative, the hygroscopic HME material may be another stage in the treatment chamber, such as a fourth stage (not shown) between the third stage 138 and the third liquid trap chamber 88. Locating the hygroscopic HME material as a fourth stage has the benefit of interacting with the exhalation gases just prior to exiting the unit 10 and recouping the moisture and heat present in the gas.

In other embodiments of the invention, the annular gas treatment section 131 may comprise a component selected from the group consisting of: (1) a filter element adapted to filter respiratory gases passing through the housing; (2) a gas permeable member adapted to exchange heat and moisture with respiratory gases passing through the housing; (3) a generating material adapted to generate water and/or heat available to humidify respiratory gases passing through the housing; (4) a hygroscopic component adapted to generate heat available to heat respiratory gases passing through the housing; (5) porous thermal mass heat exchanger material with high surface area; and (6) combinations thereof.

The second stage 136 comprises an annular tray 144 to contain the SODASORB. The ends of the annular tray 144 are designed to hold the SODASORB in the tray and permit gas flow yet inhibit fluid to flow therethrough (not shown). In a preferred embodiment, a thin layer of a porous material is sealed to the annular tray 144 ends and does not cover the annular openings (not shown) of the tray.

The third stage 138 comprises an annular spacer member 145 that extends through the third stage 138 annular opening and defines a portion of the gas flow passage 158 through the gas treatment center 131. In a preferred embodiment, spokes radiate from the patient end of the annular spacer member 145 and terminate at a circumferential ring 145a that complements the interior surface of the housing 11. The spacer member 145 and the ring 145a assist in supporting and locating the fibrous HME material 139 of the third stage and spacing the third stage 138 from the second stage 136.

Other embodiments of the invention may have more or less than three stages in the annular gas treatment section 131. Further embodiments of the invention may have a gas treatment section that is of a shape other than annular.

The exhalation bypass 132 of the treatment chamber 90 extends axially through the annular gas treatment section 131. At the patient side of the exhalation bypass is the check valve assembly 150. The check valve assembly 150 of the shown embodiment is comprised of a two part housing 152 that is circumferentially mated at joint 154. The joint 154 also crimps the radial inward extension 142 of the first stage filter 134. The check valve assembly 150 comprises an axially located leaf check valve 156 disposed in the annular gap defined by the gas treatment section first stage 134.

The exhalation bypass 132 also comprises the gas flow passage 158 extending from the check valve assembly 150 and through the annular gap defined by the second and third stages 136 and 138 of the gas treatment section 131. Other embodiments of the invention may have a gas flow passage of other configurations. Other embodiments of the invention may have other forms of check valves or may have the check valve in other locations in the gas flow passage 158.

The leaf check valve 156 inhibits inhalation gas from passing through the exhalation bypass 132. Instead of flowing through the exhalation bypass 132, substantially all of the inhalation gas flows through the gas treatment section 131. The gas treatment section 131 heats, humidifies, and filters the inhalation gas prior to being breathed in by the patient.

The leaf check valve 156 permits a portion of the patient's exhalation gas to pass through the exhalation bypass 132. By a portion of the exhalation gas passing through the exhalation bypass 132, less carbon dioxide in the exhalation air is passing through the gas treatment section 131. The useful life of the gas treatment section 131 is proportional to the amount of exhalation gas passing through it. As less exhalation gas is passing therethrough, the useful life of the gas treatment section 131 is increased by diverting a portion of the exhalation gas. The leaf check valve 156 also reduces the pressure necessary for the patient to exhale. An example of a benefit provided by reduced required exhalation pressure is easier breathing for older patient's with critical conditions.

In a preferred embodiment of the invention, the portion of the patient's exhalation gas that is diverted to the exhalation gas bypass 132 is approximately 10% to 20% of the total exhalation gas flow.

The orientation of the patient side port 12, the hole 94 in the annular baffle 92, the check valve assembly 150 and the exhalation gas bypass 132 is to enable liquid in the respiratory gas flow 2 coming from the patient to pass through the exhalation gas bypass and not contaminate the annularly positioned treatment components 135, 137 and 139. Other embodiments of the invention may have other baffle arrangements to further inhibit liquid in the respiratory gas flow from the patient from reaching the treatment components, such as partially blocking the hole 94, or having a multi-layered baffle that convolutes the gas flow, thus eliminating a linear gas flow path through the chambers 84 and 86 and increasing the opportunity for the gas flow path to impinge in a baffle and have liquid in the gas flow be disposed thereon.

Figure 6:
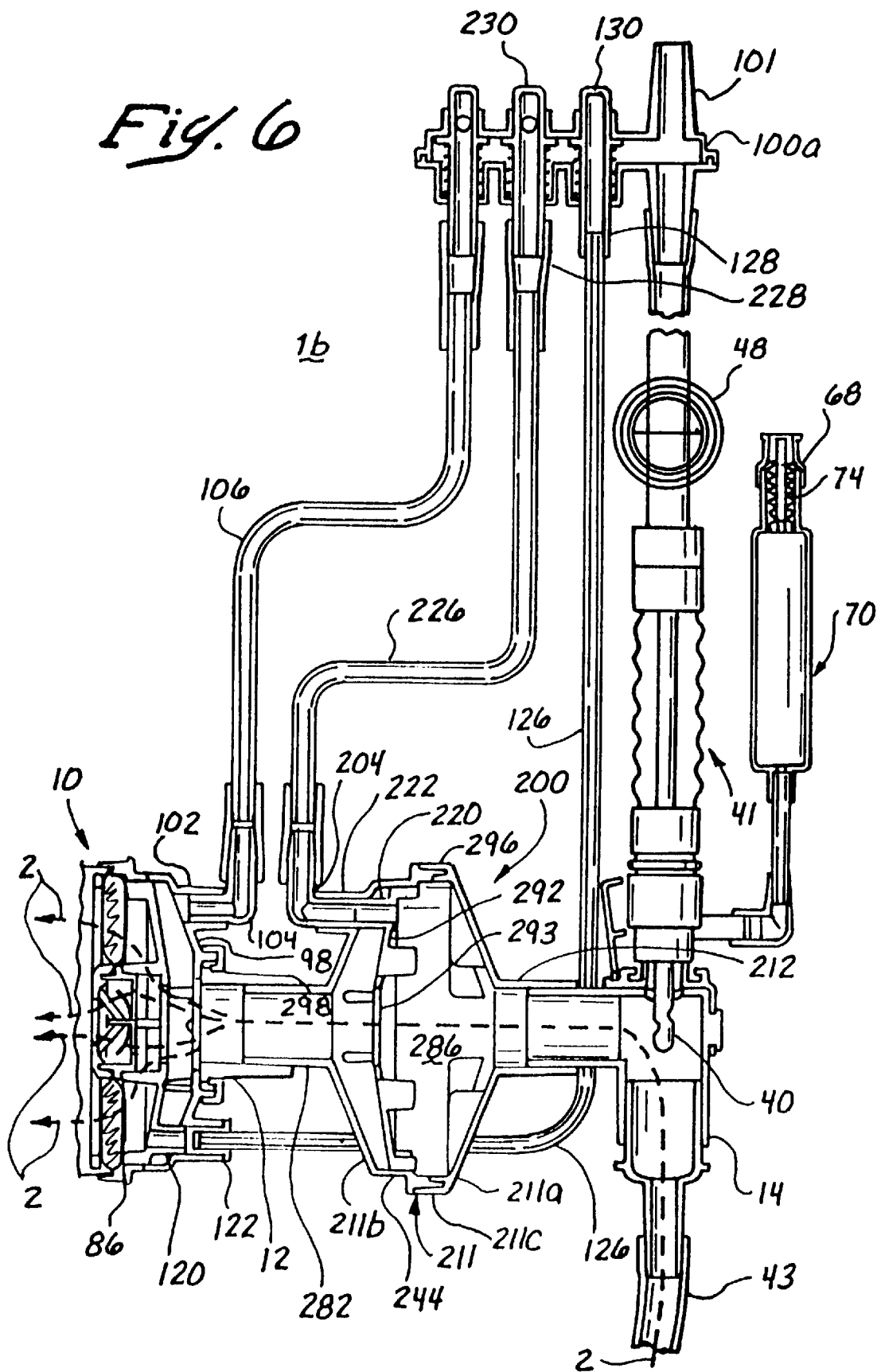
FIG. 6 is a side cross section view of the system shown in FIG. 5 with an auxiliary liquid trap inserted between the elbow fitting and the HME unit according to an embodiment of the invention.

Referring now to FIG. 6, an auxiliary mucous trap 200 is inserted between the port 12 of the HME unit 10 and the elbow fitting 14 of a respiratory treatment apparatus 1b. The respiratory treatment apparatus 1b comprises the trap 200, the HME unit 10, the ET elbow fitting 14, the suction catheter assembly 41, and a suction manifold 100a.

The auxiliary mucous trap 200 inhibits mucous from the patient from reaching the HME unit 10 and reducing the useful life thereof. The mucous trap 200 is comprised of a housing 211 containing a mucous trap chamber 286 and opposing tracheal side port 212 and treatment side port 282 extending from the housing. As is shown, the housing 211, and as a result the mucous trap chamber 286, is spaced apart from the HME unit 10 and the chambers 84, 86, and 88 disposed therein.

The auxiliary mucous trap housing 211 is comprised of a tracheal side portion 211a and a treatment side portion 211b. The portions 211a and 211b are joined with a circumferential joint 211c analogous to joint 11c. The tracheal side port 212 extends axially from the housing tracheal side portion 211a and is mated and in fluid communication with the ET elbow fitting 14. The treatment side port 282 axially extends from the housing treatment side portion 211b and is mated and in fluid commination with the HME unit patient side port 12.

The auxiliary mucous trap 200, the tracheal side port 212 and the treatment side port 282 are arranged so that respiratory flow path 2 passes between the tracheal side port and treatment side port and through the mucous trap chamber 286. The tracheal side port 212 receives respiration from the patient. The treatment side port 282 is shown receiving gas from the HME unit 10. Other embodiments of the invention may have the treatment side port 282 in fluid communication with any suitable machine or device used in respiratory treatment.

The auxiliary mucous trap 200 also comprises a baffle 292. The baffle 292 extends radially inward from a generally cylindrical side wall 296 of the housing 212. The baffle 292, the side wall 294, and the housing tracheal side portion 211a define the mucous trap chamber 286.

The baffle 292 inhibits transfer of mucous through the mucous trap 200, and thus decreases fouling and increase useful life of the HME unit 10. In the axial center of the baffle 292 is a solid center disk 293 supported by members (not shown) that radially extend toward the outer circumference of the baffle 292. The baffle 292 is concavely oriented towards the tracheal side port 212. Other embodiments of the invention may have baffles of other suitable designs and positions in the mucous trap 200.

Mucous in the patient's exhalation will predominately drain along inlet 212 walls and end 211a. However, large, air borne quantities of mucous and fluid may strike the baffle's solid center disk 293 and deposit in the mucous trap chamber 286 to be suctioned out of the mucous trap 200. The auxiliary mucous trap 200 is useful when a patient has severe mucous buildup due to breathing air with insufficient moisture and temperature or the patient is bleeding into his respiratory system. When the inhaled air of a higher humidity is inhaled, the patient may begin to expel large quantities of mucous, some of which is thick and/or highly viscous. The higher humidity air may be a result of having a humidifier that is in fluid communication with the machine side port 282. The higher humidity air may also be a result of having a heat and moisture exchange unit, such as the HME unit 10, in fluid communication with the machine side port 282. The thick and/or highly viscous may shorten or end the useful life of an attached HME unit by fouling the filters or other gas treatment components therein.

The suctioning of the mucous from the auxiliary mucous trap chamber 286 occurs in a manner similar to the suctioning of the liquid trap chambers 84, 86, and 88 of the HME unit 10. More specifically, in the preferred embodiment of the invention, the suctioning occurs in a manner similar to the liquid trap chamber 86. The baffle 292 comprises a port 220 extending toward the housing machine side portion 211b. The port 220 fluidly connects the mucous trap chamber 286 to a mucous trap opening 222 that extends through a machine side end wall 298 of the housing 211. The mucous trap opening 222 has an elbow fixture 204 extending therefrom. The elbow fixture 204 is in fluid communication with a suction manifold inlet 228 of a suction manifold 100a via a tube 226. When a valve 230 in the suction manifold 100a is opened, suction is applied to the mucous trap opening 222 via the tube 226. The suction removes mucous present in the mucous trap chamber 286.

Referring now to FIG. 5, in a preferred embodiment of the invention, a respiratory treatment apparatus 1a is assembled and used to treat a patient and reduce the opportunity for atmospheric air to enter the system unless desired. The respiratory treatment apparatus 1a comprises the HME unit 10, the suction manifold 100, ET elbow fitting 14, the suction catheter 40, and the microbial filter assembly 70. The introduction of atmospheric air into the system 1a may also introduce airborne pathogens to the patient and the treatment chamber 90. The introduction of airborne pathogens to the patient increases the opportunity of infection. The introduction of airborne pathogens into the flow path 2 between the treatment chamber 90 and the endotracheal tube 43 decreases the useful life of the treatment chamber. Further, the airborne pathogens trapped by the treatment chamber 90 may be released during an inhalation and the released pathogens may infect the patient.

The opportunity for atmospheric air to enter the respiratory treatment apparatus 1a is reduced because the system is sealed or filtered during the useful life of the treatment chamber 90. The tubes 106, 126, and 176 connecting the liquid trap chambers 84, 86, and 88 to the manifold 100 are sealed to the respective ports and manifold inlets. The microbial filter assembly 70 inhibits bacteria and other foreign matter from entering the ET elbow fitting 14 therethrough. The suction catheter system 41 is left connected to the ET elbow fitting 14 or sealed off by retracting the catheter and closing the valve before removal of the suction catheter system. In a preferred embodiment of the invention, the suction catheter fitting 42 for engaging the suction catheter system with the ET elbow fitting 14 is a bayonet fitting on a valved elbow with a sealing cap 42a for multiple treatments to be used at the endotracheal elbow fitting.

In a preferred embodiment of the invention, the respiratory treatment apparatus 1a, comprising the HME unit 10, and a suction manifold assembly comprising the suction manifold 100 and the tubes 106, 126, and 176 is disposed in a sealed container (not shown). The sealed container enables the apparatus 1a to remain clean and/or sterilized after assembly. The container may be a clear plastic bag or any other suitable container. After opening the container, the suction manifold outlet 101 is placed in fluid communication with a suction source, the patient side port 12 is placed in fluid communication with the ET elbow fitting 14, and the machine side port 82 is placed in fluid communication with a respiration machine (not shown).

During use of the apparatus to treat respiratory gases, liquid collected in the liquid trap chambers 84, 86, and 88 is removed via the suction manifold 100. Again, the applicant would like to note that for the purposes of interpreting the claims, the tubes 106, 126, and 178 may be considered a component of the suction manifold 100. To remove the liquid, a patient care taker identifies a liquid-containing trap chamber from the chambers adapted to receive liquid. The liquid in the liquid-containing trap chamber is suctioned out by opening a corresponding valve adapted to control suction through the wall opening of the liquid-containing trap chamber. The overall removal process is repeated as necessary without disconnecting the tubes 106, 126, and 178 from the suction manifold 100 or the HME unit 10. By not disconnecting the tubes, the liquid trap chambers are not exposed to the atmosphere and any pathogens located therein.

Referring now to FIG. 6, in another embodiment of the invention, the respiratory treatment apparatus 1b further comprises the auxiliary mucous trap 200. The auxiliary mucous trap 200 is preferably installed between the HME unit 10 and the ET elbow fitting 14 prior to use of the system 200.

In a further embodiment of the invention, the auxiliary mucous trap 200 of the respiratory treatment apparatus 1b may be installed after use of the invention has commenced. The necessary breaking of the connection between the HME unit patient side port 12 and the ET elbow fitting 14 to install the auxiliary mucous trap 200 does introduce atmospheric air into the system 1b. However, if the patient is producing large amounts of mucous, the relatively quick failure of the treatment chamber 90 due to contamination and successive replacements of the HME unit 10 would also result in the introduction of atmospheric air to the ET elbow fitting 14. Therefore, the insertion of the auxiliary mucous trap 200 into the system 1a not only prolongs the useful life of the HME unit 10, which is a financial benefit, but a single mucous trap insertion as opposed to repeated replacement of the HME units reduces the amount of atmospheric air to enter the patient and the opportunity of infections to develop therefrom.

Figures 7, 8:
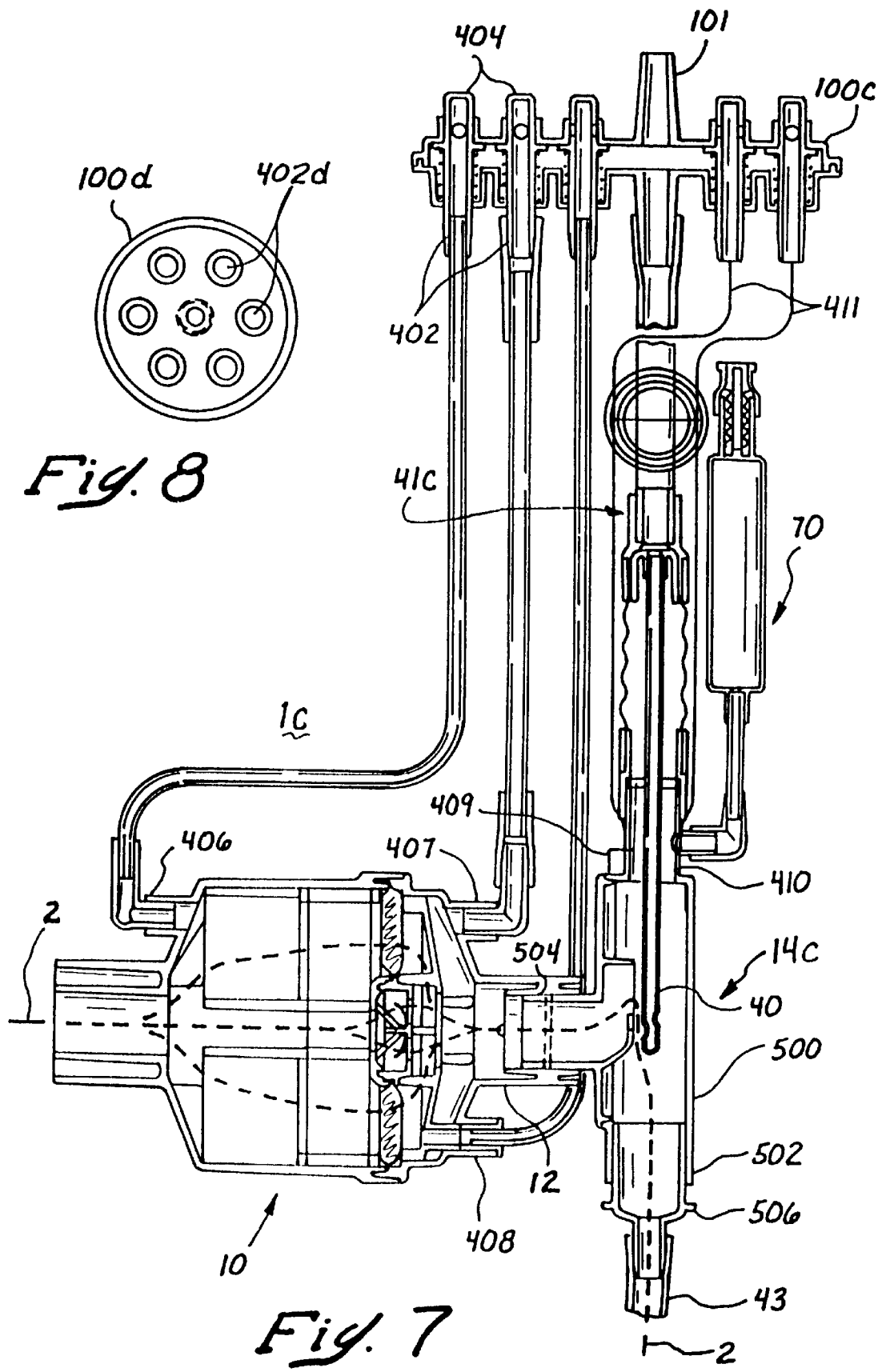
FIG. 7 is a side cross section view of a respiratory treatment system comprising an HME unit of FIG. 4 and an endotracheal suction manifold/fluid trap in fluid communication with the HME unit, a suction catheter assembly, and a tracheal tube according to an embodiment of the invention.
FIG. 8 is an end view of a circular suction manifold according to an embodiment of the invention.

Referring now to FIG. 7, a respiratory treatment apparatus 1c comprises an endotracheal suction manifold/fluid trap 14c, the heat and moisture exchange (HME) unit 10, the port 70, the suction catheter assembly 41c, and a suction manifold 100c. The endotracheal suction manifold/fluid trap 14c may also be referred to as an endotracheal suction manifold. The suction manifold 100c comprises five suction inlets 402 and valves 404. The suction inlets 402 are in fluid communication with ports 406–410 in the apparatus 1c. The ports 406–408 are in fluid communication with the HME unit 10. The ports 409–410 are in fluid communication with the endotracheal suction manifold/fluid trap 14c as described below.

The five suction inlets 402 of the suction manifold 100c of the respiratory treatment apparatus 1c is arranged in a linear fashion in the embodiment of the invention shown in FIG. 7. Other embodiments of the invention may have other arrangements of the inlets 402. Referring specifically to FIG. 8, an embodiment of the invention may have a circular suction manifold 100d with the inlets 402d being arranged in a circular fashion. Other embodiments of the invention may have square, oval, rows, or three dimensional arrangements of the suction manifold and the inlets.

Referring now to FIGS. 9a–c as well, the endotracheal suction manifold/fluid trap 14c functions as the ET elbow fitting 14 previously described and as a fluid trap for receiving fluid from the respiratory gases passing therethrough. The endotracheal suction manifold/fluid trap 14c comprises a housing 500 with multiple ports. Two of the ports are a patient side opening 502 and a machine side opening 504. A ET fitting 506 is disposed between the patient side opening 502 and a tracheal tube 43 to provide fluid communication therebetween. The machine side opening 504 extends from the housing 500 in a generally perpendicular direction to the patient side opening 502. The machine side opening 504 is in fluid communication with the HME unit 10 in an embodiment of the invention. Other embodiments of the invention may be in fluid communication with other respiratory gas treatment devices. The respiratory flow path 2 extends through the housing 500 between the openings 502 and 504.

The endotracheal suction manifold/fluid trap 14c also has a suction catheter assembly opening 508 that is in fluid communication with a suction catheter assembly 41. The catheter assembly opening 508 is linearly aligned with the patient side opening 502 to facilitate extending the suction catheter 40 from the assembly through the housing 500, the patient side opening 502, the fitting 506, and into the tracheal tube 43. The remaining two ports in the shown embodiment of the invention are the suction ports 409 and 410, which are described in more detail below.

An additional port, a lavage port 413, is shown in fluid communication with the catheter assembly opening 508. The lavage port 413 is adapted to receive saline or other solution to perform a tracheal lavage. Other embodiments of the invention may have a lavage port disposed elsewhere on the endotracheal suction manifold/fluid trap 14c. Still other embodiments of the invention may have other ports for other purposes.

In the shown embodiment of the invention, the housing 500 has the shape of a six sided box with two opposing sides 512 and 514 that are generally trapezoidal in shape. The machine side opening 504 extends from side 514 in FIGS. 9a–c.

Extending inwardly from the housing side 514 is an interior housing 516. The interior housing 516 has a first open end 518 in fluid communication with the machine side opening 504. The interior housing 516 has a second open end 520 that opposes the first open end 518 while being offset from it. As a result, the second open end 520 is elevated above the housing side 514.

The inwardly extending interior housing 516 and an interior surface 522 of the housing 500 define a fluid trap 524. The fluid trap 524 traps fluid entering the trap via the tracheal tube. The endotracheal elbow fittings and endotracheal suction manifolds disclosed in the prior art do not trap consequential amounts of fluid for removal by suction, resulting in fluid either moving through the fitting or manifold and contaminating a respiratory treatment device or flowing back into the patient—both of which are undesirable.

In the preferred embodiment of the invention, the fluid trap 524 holds approximately 5 cc's of fluid in any orientation before the mucous overflows and exits the trap through the machine side opening 504. Other embodiments of the invention may have baffles in the housing 500 to assist in knocking out the fluid, may or may not have an elevated opening 520 or equivalent thereof, may have the machine side opening positioned such that while in use the opening is vertically oriented at the top portion of the trap, and other suitable configurations.

The fluid contained in the endotracheal suction manifold/ fluid trap 14c is removed without exposing the interior of the trap, and therefore the respiratory flow path 2 and the patient, to the atmosphere and risk contamination and infection, by suction through the outlets 409 and 410. The outlets 409 and 410 are in fluid communication with the suction manifold 100c via tubes 411. By opening the appropriate valves 404 in the suction manifold 100c, the mucous is withdrawn from the trap 14c.

The suction outlets 409 and 410 of the elbow endotracheal suction manifold/fluid trap 14c are located on a side 530 of the housing 500 from which extends the catheter assembly opening 508 in the shown embodiment of the invention. Referring specifically to FIG. 9b, the suction outlets are located in opposing corners 532 of the housing side 530 to facilitate removing fluid from the trap 524 regardless of the trap orientation. Other embodiments of the invention may have other suitable arrangements of the suction outlets or a differing amount of suction outlets.

The function of the endotracheal suction manifold/fluid trap 14c is to trap and remove mucous from gases flowing from the patient along the respiratory flow path 2 before the mucous contaminates the HME unit 10. The endotracheal suction manifold/fluid trap 14c does not fully resemble ET elbow fittings known in the prior art used for directing the respiratory flow path 2 and permitting the suction catheter assembly 41 to be functional attached thereto, an example of which is the ET elbow fitting 14. However, the function of the trap 14c is to remove mucous exiting the patient, permit functional attachment of the suction catheter assembly 41 thereto, and direct gases therethrough along the respiratory flow path 2. Any device or combination of devices which accomplishes these functions is equivalent.

The endotracheal suction manifold/fluid trap 14c, and equivalent invention embodiments thereof, may eliminate the need for breaching the respiratory treatment apparatus 1c to install the auxiliary mucous trap 200. The trap 524 may be sufficient to contain expelled fluid, reducing contamination and extending the useful life of the HME unit 10. Further, by reducing the breaching of the apparatus 1c, the useful life of the HME unit 10 is increased and the opportunity for infecting the patient is reduced.

Other embodiments of the invention may incorporate into one integral unit a suction catheter assembly, a mucous trap, and a respiratory flow path direction means for directing the respiratory gas flow between the patient and a respiratory treatment device. The respiratory treatment device may be the HME unit or any other suitable apparatus, system, machine, or combination thereof.

Figure 10A:
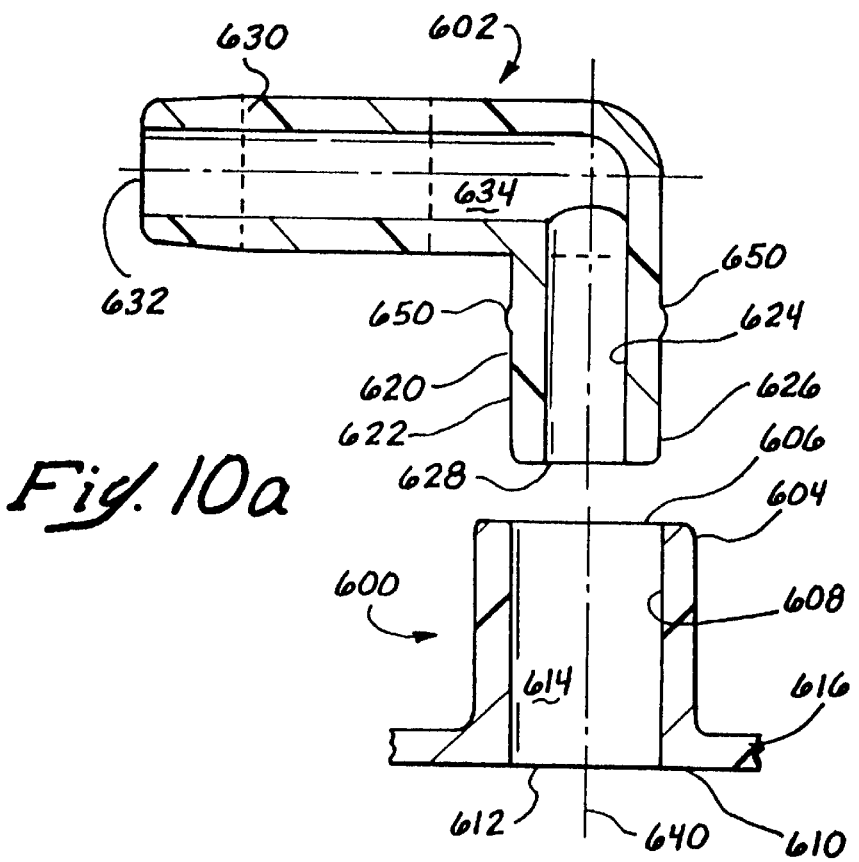
FIGS. 10a–b are cross section views of an unassembled and an assembled swivel fitting, respectively.
Figure 10B:
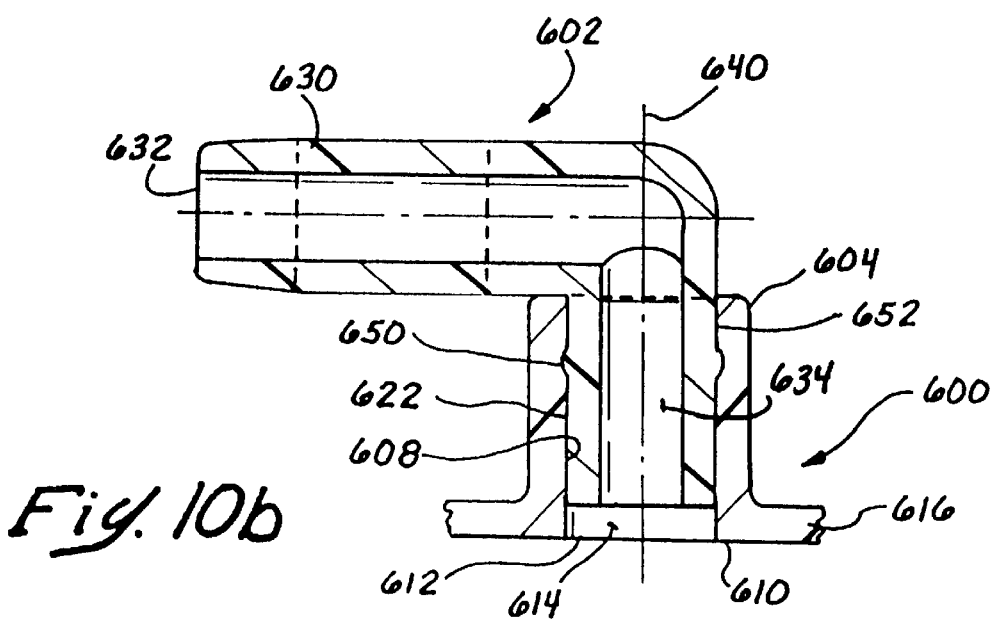

Referring now to FIGS. 10a and 10b, a female suction outlet 600 is mated with a hollow L-shaped male swivel joint 602 such that the mated parts swivel easily and create a seal. By being able to swivel easily, the orientation of a suction tube (not shown) mated to the male swivel joint 602 may easily be changed. Being able to change the suction tube orientation is a benefit in arranging the suction tubes on the patient.

The female suction outlet 600 comprises a mating end 604 with a mating end opening 606 extending therethrough. Extending from the mating end 604 is an interior surface 608 that terminates at an opposing end 610 with an opposing end opening 612 extending therethrough. The interior surface 608, the mating end opening 606 and the opposing end opening 612 define a female portion interior 614. The female suction outlet 600 is shown extending from a house wall 616 with the opposing end 610 aligned with the wall. Other embodiments of the invention may have any portion of the female suction outlet 600 aligned with the wall 616, including the mating end 604.

The L-shaped male swivel joint 602 comprises a continuous wall 620 with an exterior surface 622 and an interior surface 624. The continuous wall 620 has a distal end 626 with a distal end opening 628 therethrough. The continuous wall 620 also has an opposing proximal end 630 having a proximal end opening 632 therethrough. The distal and proximal ends 626 and 630 are shown at right angles to each other, but other embodiments of the invention may have the two ends oriented at any other angle, including 180 degrees. The distal end opening 628, the continuous wall interior surface 624, and the proximal end opening 632 define a gas flow passage 634 through the male swivel joint 602.

The continuous wall exterior surface 622 complements the female outlet interior surface 608. The male swivel joint 602 and the female suction outlet 600 being adapted such that upon insertion of the distal end 626 through the mating end opening 606 and into the female portion interior 614, the male exterior surface 622 contacts the female interior surface 608, as shown in FIG. 10b. The male swivel joint 602 is rotatable relative to the female suction outlet 600 about an axis 640 extending through the female portion interior 614 and between the mating end opening 606 and the opposing end opening 612.

A circumferential bead 650 radially extends from the male swivel joint exterior surface 622. The bead 650 defines a plane (not shown) that is normal to the axis 640 when the male swivel joint 602 is mated to the female suction outlet 600. The bead 650 and the female interior surface 608 are adapted such that upon insertion of the male swivel joint 602 into the female suction outlet, the bead 650 forms a bead deformation undercut 652 in the female interior surface 608. This occurs as the bead 650 deforms the female interior surface 608 as the bead is comprised of harder material than the female suction outlet. In preferred embodiments of the invention, the suction outlet 600 may be formed of a butadiene/styrene mixture, as is sold under the trademark PHILLIPS PETROLEUM K-RESIN PLASTIC, while the bead 650 and the male swivel joint 602 may be formed of harder grade of plastic such as acrylic, ABS, or polycarbonate, that retains it shape under the compression from the female suction outlet 600.

In a preferred embodiment of the invention, the female interior surface 608 and the male exterior surface 622 are tapered. In a more preferred embodiment of the invention, the taper is less that two degrees per side. In a more preferred embodiment of the invention, the taper is between 0.5 and 0.72 degrees per side. The advantage of the relatively low taper is the ability of the male and female parts to be more tightly held by increasing the distance the male part is inserted into the female part—or as in the shown example, the distance the male swivel joint 602 may be inserted into the female suction outlet 600. However, the further the male swivel joint 602 is inserted into the female suction outlet 600, the more force is needed to rotate the two parts due to the increased friction therebetween. The amount of the insertion may be limited by a stop. In the shown embodiment, proximal end 630 of the male swivel joint 602 acts as a stop because it is at a ninety degree angle with the male swivel joint distal end 626. In other embodiments of the invention, the surfaces 608 and 622 may be cylindrical. However, the additional frictional force between cylindrical male and female parts increases only linearly as a function of the distance of insertion, as opposed to the exponential increase in frictional force obtained with the tapered fittings.

As a result of the bead 650 forming the bead deformation undercut 652 in the female suction outlet interior surface 608, a seal and a retaining force to inhibit axial movement between the two is created and maintained. The outlet 600 and the joint 602 are held together by the bead/bead deformation undercut. The outlet 600 and the joint 602 is not forced apart by the pressures generated in the respiratory gas treatment devices in which the outlet/joint is used because the pressures are approximately two pounds per square inch gage maximum. Gases and liquids may flow through the outlet/joint via the female portion interior 614 and the joint gas flow passage 634. The interior of respiratory gas treatment device is protected from exposure to the ambient atmosphere by the bead and the bead deformation undercut.

In an embodiment of the invention, the male swivel joint 602/female suction outlet 600 may be used to fluidly connect tubes of a suction manifold to a housing (not shown). The proximal end opening 632 of the male swivel joint 602 is fluidly connected to a tube of the suction manifold. The female suction outlet 600 extends from a housing wall and the joint 602 is mated to the outlet. Other embodiments of the invention may have the male portion attached to the housing and the female portion attached or incorporated into the tube.

In an embodiment of the invention, the male swivel joint 602/female suction outlet 600 may be used to fluidly connect any two respiratory treatment devices. An example of such an application may be used to fluidly connect either of patient side port 12 or the machine side port 82 of the HME unit 10 (see FIG. 5) to another respiratory device such as an ET elbow fitting, an endotracheal suction manifold, a combined endotracheal suction manifold/liquid trap, a respiratory machine, or an auxiliary trap. The male swivel joint 602/female suction outlet 600 may also be used to connect a suction catheter assembly to an endotracheal suction manifold.

Figure 11A:
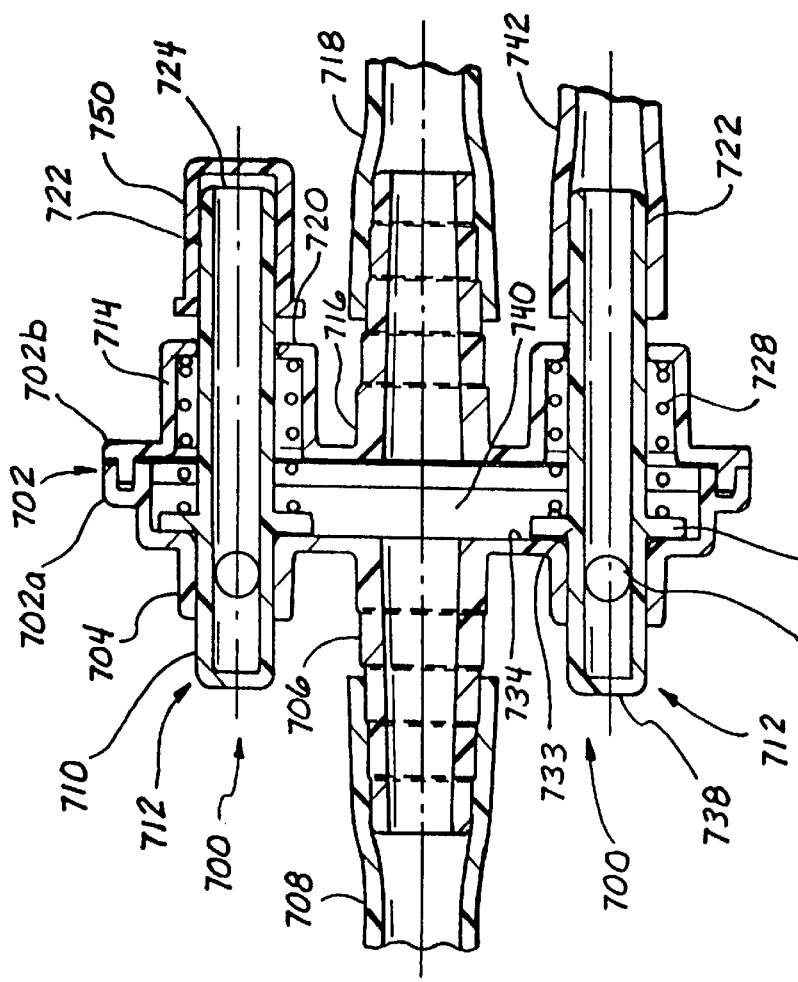
FIGS. 11a–b are views of a suction valve assembly.
Figure 11B:
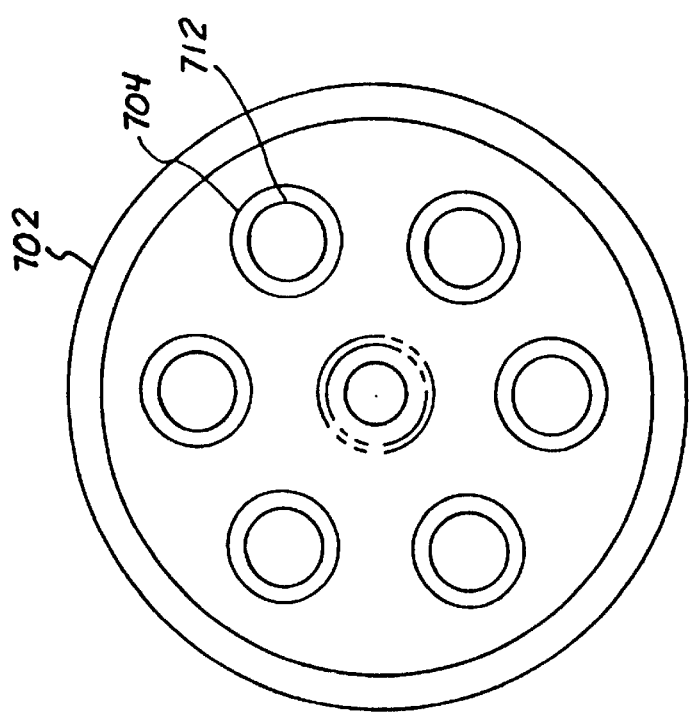

Referring now to FIGS. 11a and 11b, details of a preferred embodiment of the suction manifold valves 700 are shown. In terms of explanation, shown on the right side of the drawing is the side proximal to a suction source (not shown) and shown to the left side of the drawing is the side distal from the suction source.

The suction manifold valves 700 are functionally disposed in a suction manifold housing 702. The suction manifold housing 702 is disk shaped as shown in FIG. 11b. The suction manifold housing 702 comprises a proximal part 702a and a distal part 702b which when attached forms the housing. The assembled housing 702 is hollow to enable gas and liquid to flow therethrough.

The suction manifold housing proximal part 702a comprises six circular proximal lips 704 that extend proximally from the housing. The lips 704 are arranged in a circular fashion about a centrally located proximal port 706. The proximal port 706 has a stepped exterior surface to assist in securing a tube 708 thereto. The tube 708 is functionally connected to a suction source (not shown). Extending out from the proximal lips 704, respectively, are actuation ends 710 of spools 712, which are discussed in detail below.

The suction manifold housing distal part 702b comprises six circular distal lips 714 that extend distally from the housing. The lips 714 are arranged in a circular fashion about a centrally located distal port 716 that opposes the proximal port 706. The distal port 716 has a stepped exterior surface to assist in securing a suction catheter system 718 thereto. The distal lips 714 also extend distally from the housing 702 and respectively oppose the proximal lips.

At the distal end of the distal lips 714 are inwardly extending flanges 720 that complement the distal end 722 of the spools 712. The valve seal occurs on a narrow chamfer at the intersection of the flange 732 and the spool 712 that is in contact with the housing 702a when the valve 700 is closed.

The spools 712 are hollow with a distal axial opening 724 and a proximal radial opening 726. The spools 712 are shown in a closed position such that the radial opening 726 is sealed by the proximal lips 704. The spools 712 are urged into this position by a spring 728 that is disposed in the housing 702. The spring 728 surrounds a portion of the spool and urges a radial flange 732 that extends from the spool away from the inwardly extending flange 720 of the distal lip 714. This arrangement results in the chamfer between the flange 732 and the spool 712 being urged into contact against the corner 733 formed by the interior surface 734 of the housing proximal part 702a and the proximal lip 704.

To open the suction valve 700, actuation contact surfaces 738 at the ends of the actuation ends 710 of spools 712 are depressed. The resulting translation of the spools 712 aligns the spools radial openings 726 with the hollow interior 740 of the housing 702. The aligning of the openings 726 with the housing interior 740 results in opening a gas and fluid flow path between the spool axial opening 724 and the suction source.

The suction that is created when the suction valve 700 is opened is used to remove mucous and other fluids from liquid traps (not shown). The axial opening 724 is in fluid communication with the liquid traps via a tube 742 shown inserted over the distal end 722 of the spool 712. A cap 750 may also be placed about the distal end 722 of the spool 712 to seal the axial opening 724.

The suction manifold housing 702 and the spools 712 are designed to create seals where the spools extend from the housing. In a preferred embodiment of the invention, the lips 704 and 714 are elastic enough to assist in conforming the lips to the spool 712. Examples of suitable materials for the lips 704 and 714 are butadiene/styrene copolymer, polyethylene, polypropylene, and a polyethylene/polypropylene copolymer. The spool 712 would be made of a relatively non-elastic material, such as polycarbonate, in this embodiment of the invention.

In other embodiments of the invention, the housing 702 may be of other shapes, the spools may be of other shapes, the housing may be of other construction, the lips 704, 714, and ports 706 and 716 may be disposed in other arrangements. The tubes 742 and the corresponding spools 712 may be color matched to assist the care giver in selecting the proper valve 700 to open.

While this invention has been described with respect to various specific examples and embodiments, it is to be understood that the invention is not limited thereto and that it can be variously practiced within the scope of the following claims.

What is claimed is:

1. An apparatus for treating the respiratory gases of a patient, the apparatus comprising a housing comprising:
   a) a patient side port adapted for passing respiratory gases between the housing and the patient;
   b) a machine side port adapted for passing respiratory gases between the housing and a respiration machine;
   c) two or more liquid trap chambers adapted to receive liquid;
   d) a treatment chamber containing a treatment component adapted to provide a benefit to the respiratory gases passing therethrough, wherein the patient side and machine side ports, the treatment chamber, and the liquid trap chambers are positioned to define a respiratory flow path through the housing passing between the patient side and machine side ports and through the treatment chamber and the liquid trap chambers; and
   e) a wall having one or more openings through which liquid is removable from the liquid trap chambers, wherein the one or more openings are spaced apart from the patient side port and the machine side port and the liquid trap chambers are configured to inhibit liquid passed from outside the housing through the patient side port from entering the treatment chamber.

2. The apparatus of claim 1, wherein the liquid trap chambers are sized and positioned to hold liquid passed from outside the housing through the patient side port.

3. The apparatus of claim 1, wherein the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water and/or heat available to humidify respiratory gases passing through the housing; (4) a hygroscopic component adapted to generate heat available to heat respiratory gases passing through the housing; (5) porous thermal mass heat exchanger material with high surface area; and (6) combinations thereof.

4. The apparatus of claim 1, wherein at least one of the liquid trap chambers is sized and positioned to collect liquid between the treatment chamber and the patient side port.

5. The apparatus of claim 1, wherein the treatment chamber further comprises a gas flow bypass extending through the treatment chamber, wherein the gas flow bypass is linearly aligned with the patient side port.

6. The apparatus of claim 5, further comprising a check valve in fluid communication with the gas flow bypass, the check valve adapted to inhibit gas flow from the machine side port, through the gas flow bypass, and to the patient side port and adapted to enable a portion of gas flow or liquid flow from the patient side port to flow through the gas flow bypass and towards the machine side port, with the remainder of the gas flow from the patient side port being directed through the treatment chamber.

7. The apparatus of claim 6, further comprising a baffle disposed between the patient side port and the treatment chamber, wherein the patient side port, the gas flow bypass, and a hole in the baffle are linearly aligned.

8. The apparatus of claim 6, wherein the check valve is a leaf check valve.

9. An apparatus for treating the respiratory gases of a patient, the apparatus comprising:
   a) a housing comprising:
      i) a patient side port adapted for passing respiratory gases between the housing and the patient;
      ii) a machine side port adapted for passing respiratory gases between the housing and a respiration machine;
      iii) one or more liquid trap chambers adapted to receive liquid;
      iv) a treatment chamber containing a treatment component adapted to provide a benefit to the respiratory gases passing therethrough, wherein the patient side and machine side ports, the treatment chamber, and the liquid trap chambers are positioned to define a respiratory flow path through the housing passing between the patient side and machine side ports and through the treatment chamber and the liquid trap chambers; and
      v) a wall having one or more openings through which liquid is removable from the liquid trap chambers, wherein the one or more openings are spaced apart from the patient side port and the machine side port; and
   b) a suction assembly in fluid communication with the one or more openings and adapted to remove liquid from liquid trap chambers without exposing the respiratory flow path through the housing to ambient atmosphere, the suction assembly comprises a suction manifold comprising:
      1) one or more inlets in fluid communication with the one or more liquid trap chambers, respectively;
      2) an outlet adapted for connection to a suction source; and
      3) one or more valves disposed between the one or more wall openings and the suction manifold outlet, wherein the valves are adapted to control suction through the one or more wall openings.

10. The apparatus of claim 9, wherein the liquid trap chambers are configured to inhibit liquid passed from outside the housing through the patient side port from entering the treatment chamber.

11. The apparatus of claim 9, wherein the liquid trap chambers are sized and positioned to hold liquid passed from outside the housing through the patient side port.

12. The apparatus of claim 9, wherein the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water and/or heat available to humidify respiratory gases passing through the housing; (4) a hygroscopic component adapted to generate heat available to heat respiratory gases passing through the housing; (5) porous thermal mass heat exchanger material with high surface area; and (6) combinations thereof.

13. The apparatus of claim 9, wherein at least one of the liquid trap chambers is sized and positioned to collect liquid between the treatment chamber and the patient side port.

14. The apparatus of claim 9, wherein at least one of the liquid trap chambers is sized and positioned to collect liquid between the treatment chamber and the machine side port.

15. The apparatus of claim 9, wherein:
a) a first liquid trap chamber is sized and positioned to collect liquid between the treatment chamber and the patient side port; and
b) a second liquid trap chamber is sized and positioned to collect liquid between the treatment chamber and the machine side port.

16. The apparatus of claim 15, wherein a third liquid trap container is sized and positioned to collect liquid between the treatment chamber and the first liquid trap chamber.

17. The apparatus of claim 16, further comprising a baffle disposed between the first and third liquid trap chambers.

18. The apparatus of claim 17, wherein the baffle is of an annular shape.

19. The apparatus of claim 9, wherein the treatment chamber further comprises a gas flow bypass extending through the treatment chamber, wherein the gas flow bypass is linearly aligned with the patient side port.

20. The apparatus of claim 19, further comprising a check valve in fluid communication with the gas flow bypass, the check valve adapted to inhibit gas flow from the machine side port, through the gas flow bypass, and to the patient side port and adapted to enable a portion of gas flow from the patient side port to flow through the gas flow bypass and towards the machine side port, with the remainder of the gas flow from the patient side port being directed through the treatment chamber.

21. The apparatus of claim 20, further comprising a baffle disposed between the patient side port and the treatment chamber, wherein the patient side port, the gas flow bypass, and a hole in the baffle are linearly aligned.

22. The apparatus of claim 20, wherein the check valve is a leaf check valve.

23. A system for treating the respiratory gases of a patient, the system comprising;
a) a liquid trap comprising:
i) a trap housing having a patient side port being adapted for fluid communication with a tracheal tube device, and a machine side port being adapted for fluid communication with a device comprising a respiratory gas treatment chamber; and
ii) a trap chamber positioned in the trap housing between the patient side port, the machine side port, the trap chamber being adapted to receive liquid; and
iii) wherein a respiratory gas treatment chamber is not present in the trap housing; and
iv) a baffle disposed in the trap housing, the baffle being adapted to be impinged upon by a respiratory gas flow passing between the patient side port and the machine side port and through the housing; and
b) a device comprising the respiratory gas treatment chamber comprising a housing comprising:
i) a patient side port adapted for passing respiratory gases between the device housing and the patient; and
ii) a machine side port adapted passing respiratory gases between the device housing and a respiration machine;
iii) wherein the respiratory gas treatment chamber contains a treatment component adapted to provide a benefit to the respiratory gases passing therethrough;
iv) wherein the device patient side port, the device machine side port, and the respiratory gas treatment chamber are positioned to define a respiratory flow path through the device housing passing between the device patient side port and device machine side port and through the treatment chamber;
c) wherein the machine side port of the trap housing is in fluid communication with the patient side port of the device comprising the respiratory gas treatment chamber, wherein the trap housing is spaced apart from the housing of the device comprising the respiratory gas treatment chamber.

24. The system of claim 23:
a) wherein the trap housing comprises a wall having an opening through which liquid is removable from the trap chamber, wherein the opening is spaced apart from the trap housing patient side and machine side ports; and
b) the system further comprises a suction assembly in fluid communication with the opening and adapted to remove liquid from liquid trap chamber without exposing the respiratory flow path through the trap housing to ambient atmosphere.

25. The system of claim 24, wherein the suction assembly comprises:
a) a suction manifold comprising an inlet in fluid communication with the trap chamber and an outlet adapted for connection to a suction source; and
b) a valve disposed between the wall opening and the suction manifold outlet, wherein the valve is adapted to control suction through the wall opening.

26. The system of claim 23, wherein the baffle comprises a blocking member positioned in a direct path between the patient side port and the machine side port.

27. The system of claim 24, wherein:
a) the housing of the device comprising the respiratory gas treatment chamber further comprises
i) one or more device liquid trap chambers for receiving liquid, the device liquid trap chambers being disposed in the respiratory flow path therethrough; and
ii) device openings in a device wall through which liquid is removable from the device liquid trap chambers;
b) the suction assembly is in fluid communication with the device openings and adapted to remove liquid from the device liquid trap chamber without exposing the respiratory flow path through the trap housing to ambient atmosphere.

28. The system of claim 27, wherein the suction assembly is adapted to facilitate periodic removal of liquid from the device liquid trap chambers and the trap chamber of the liquid trap without exposing the device liquid trap chambers and the trap chamber of the liquid trap to the atmosphere outside of the device and the liquid trap.

29. The system of claim 27, wherein the suction assembly is adapted to facilitate periodic removal of liquid from the device liquid trap chambers and the trap chamber of the liquid trap without separating the suction manifold from the device wall openings and the liquid trap wall opening.

30. A respiratory gas treatment system comprising an endotracheal suction manifold comprising:
a) a device port adapted for connection with a respiratory treatment device;
b) a patient side port adapted for passing respiratory gases between the endotracheal suction manifold and the patient;
c) a machine side port adapted passing respiratory gases between the endotracheal suction manifold and a respiration machine;

d) a liquid trap adapted to receive liquid, wherein the patient side port, the machine side port, and the liquid trap is positioned to define a respiratory flow path through the endotracheal suction manifold passing between the patient side and machine side ports and through the liquid trap;

e) a wall having an opening through which liquid is removable from the liquid trap, wherein the opening is spaced apart from the patient side port and the machine side port;

f)
  a) a suction manifold comprising:
    i) an endotracheal inlet in fluid communication with the liquid trap; and
    ii) an outlet adapted for connection to a suction source; and
  b) a valve disposed between the wall opening and the suction manifold outlet, wherein the valve is adapted to control suction through the wall opening.

31. The system of claim 30, further comprising a suction catheter assembly connected to the device port.

32. The system of claim 30, further comprising an apparatus for use during tracheal lavages connected to the device port, the apparatus comprising:
  a) a housing having a first port and a second port, the first port being positioned to receive a lavaging liquid, the second port being in fluid communication with a tracheal tube in fluid communication with the patient side port; and
  b) a microbial filter disposed in the housing, wherein first and second ports and the microbial filter are positioned so that gas or lavaging liquid passes from the first port to the second port and through the microbial filter.

33. The system of claim 30, further comprising an apparatus for treating the respiratory gases of a patient, the apparatus comprising a housing comprising:
  a) a housing patient side port connected to the machine side port of the endotracheal suction manifold, the housing patient side port being adapted for passing respiratory gases between the housing and the patient;
  b) a housing machine side port adapted for passing respiratory gases between the housing and the respiration machine;
  c) a treatment chamber containing a treatment component adapted to provide a benefit to the respiratory gases passing therethrough;
  d) a housing liquid trap adapted to receive liquid from the respiratory gases passing therethrough, wherein the housing patient side port, the housing machine side port, the housing treatment chamber, and the housing liquid trap are positioned to define a respiratory flow path through the housing passing between the housing patient side and housing machine side ports and through the treatment chamber and the housing liquid trap; and
  e) a housing wall having an opening through which liquid is removable from the housing liquid trap;
  f) wherein the suction manifold further comprises an apparatus inlet in fluid communication with the housing liquid trap through the housing wall opening;
  g) wherein the system further comprises an apparatus valve disposed between the housing wall opening and the suction manifold outlet, wherein the apparatus valve is adapted to control suction through the housing wall opening.

34. A method for providing respiratory gases to a patient comprising the steps of:
  a) providing a closed container which contains an apparatus comprising:
    i) a housing comprising:
      a patient side port adapted for passing respiratory gases between the housing and the patient;
      a machine side port adapted passing respiratory gases between the housing and a respiration machine;
      one or more liquid trap chambers adapted to receive liquid;
      a treatment chamber containing a treatment component adapted to provide a benefit to the respiratory gases passing therethrough, wherein the patient side and machine side ports, the treatment chamber, and the liquid trap chambers are positioned to define a respiratory flow path through the housing passing between the patient side and machine side ports and through the treatment chamber and the liquid trap chambers; and
      a wall having one or more openings through which liquid is removable from the liquid trap chambers;
    ii) a suction assembly in fluid communication with the one or more openings and adapted to remove liquid from liquid trap chambers without exposing the respiratory flow path through the housing to ambient atmosphere;
  b) opening the container;
  c) placing the suction assembly in fluid communication with a suction source;
  d) placing the patient side port in fluid communication with a patient; and
  e) placing the machine side port in fluid communication with a respiration machine.

35. The method of claim 34, further comprising the steps of:
  a) identifying a liquid-containing liquid trap chamber from the one or more liquid trap chambers adapted to receive liquid;
  b) using the suction assembly to suction liquid from the liquid-containing liquid trap chamber; and
  c) repeating the identifying and using steps without exposing the liquid trap chambers to the ambient atmosphere.

36. The method of claim 34, further comprising the step of installing an auxiliary liquid trap chamber between the patient side port and the patient such that the apparatus and the auxiliary liquid trap chamber is in fluid communication with the patient, wherein the auxiliary liquid trap chamber is spaced apart from the apparatus housing.

37. The method of claim 34, further comprising the step of installing a combined endotracheal suction manifold/fluid trap between the patient side port and the patient such that the apparatus and the endotracheal suction manifold/fluid trap is in fluid communication with the patient.

38. An apparatus for treating the respiratory gases of a patient, the apparatus comprising a housing comprising:
  a patient side port adapted for passing respiratory gases between the housing and the patient;
  a machine side port adapted for passing respiratory gases between the housing and a respiration machine;
  a treatment chamber containing a treatment component adapted to provide a benefit to the respiratory gases passing therethrough, the treatment component is selected from the group consisting of: a filter element adapted to filter respiratory gases passing through the housing; a gas permeable member adapted to exchange heat and moisture with respiratory gases passing through the housing; and combinations thereof; and a gas flow bypass extending through the treatment chamber, wherein the gas flow bypass is positioned so that a portion of the gases passing from the patient through the housing passes through the gas flow bypass.

39. The apparatus of claim 38, further comprising a check valve in fluid communication with the gas flow bypass, the check valve adapted to inhibit gas flow from the machine side port through the gas flow bypass to the patient side port, and further adapted to enable a portion of gas flow or liquid flow from the patient side port to flow through the gas flow bypass and towards the machine side port.

40. The apparatus of claim 39 wherein the treatment component is the filter element.

41. The apparatus of claim 39 wherein the treatment component is the gas permeable member.

42. The apparatus of claim 39 wherein the treatment component is a combination of the filter element and the gas permeable member.

43. The apparatus of claim 39, wherein the check valve is a leaf check valve.

44. An apparatus for treating the respiratory gases of a patient, the apparatus comprising a housing comprising:

a) a patient side port adapted for passing respiratory gases between the housing and the patient;

b) a machine side port adapted for passing respiratory gases between the housing and a respiration machine;

c) two or more liquid trap chambers adapted to receive liquid;

d) a treatment chamber containing a treatment component adapted to provide a benefit to the respiratory gases passing therethrough, wherein the patient side and machine side ports, the treatment chamber, and the liquid trap chambers are positioned to define a respiratory flow path through the housing passing between the patient side and machine side ports and through the treatment chamber and the liquid trap chambers; and e) a wall having one or more openings through which liquid is removable from the liquid trap chambers, wherein the openings are spaced apart from the patient side port and the machine side port and at least one of the liquid trap chambers is sized and positioned to collect liquid between the treatment chamber and the machine side port.

45. The apparatus of claim 44, wherein:

a) a first liquid trap chamber is sized and positioned to collect liquid between the treatment chamber and the patient side port; and b) a second liquid trap chamber is sized and positioned to collect liquid between the treatment chamber and the machine side port.

46. The apparatus of claim 45, wherein a third liquid trap container is sized and positioned to collect liquid between the treatment chamber and the first liquid trap chamber.

47. The apparatus of claim 46, further comprising a baffle disposed between the first and third liquid trap chambers.

48. The apparatus of claim 47, wherein the baffle is of an annular shape.

49. A respiratory gas treatment system comprising an endotracheal suction manifold comprising:

a) a device port adapted for connection with a respiratory treatment device;

b) a patient side port adapted for passing respiratory gases between the endotracheal suction manifold and the patient;

c) a machine side port adapted passing respiratory gases between the endotracheal suction manifold and a respiration machine;

d) a liquid trap adapted to receive liquid, wherein the patient side port, the machine side port, and the liquid trap is positioned to define a respiratory flow path through the endotracheal suction manifold passing between the patient side and machine side ports and through the liquid trap;

e) a wall having an opening through which liquid is removable from the liquid trap, wherein the opening is spaced apart from the patient side port and the machine side port; and apparatus for use during tracheal lavages connected to the device port, the apparatus comprising:

i) a housing having a first port and a second port, the first port being positioned to receive a lavaging liquid, the second port being in fluid communication with a tracheal tube in fluid communication with the patient side port; and ii) a microbial filter disposed in the housing, wherein the first and second ports and the microbial filter are positioned so that gas or lavaging liquid passes from the first port to the second port and through the microbial filter.

* * * * *